United States Patent
Moore

(10) Patent No.: US 11,783,480 B2
(45) Date of Patent: *Oct. 10, 2023

(54) SEMI-AUTOMATED SYSTEM FOR REAL-TIME WOUND IMAGE SEGMENTATION AND PHOTOGRAMMETRY ON A MOBILE PLATFORM

(71) Applicant: KCI Licensing, Inc., San Antonio, TX (US)

(72) Inventor: Brett L. Moore, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 17/697,718

(22) Filed: Mar. 17, 2022

(65) Prior Publication Data

US 2022/0207736 A1 Jun. 30, 2022

Related U.S. Application Data

(63) Continuation of application No. 16/986,878, filed on Aug. 6, 2020, now Pat. No. 11,315,245, which is a continuation of application No. 16/308,158, filed as application No. PCT/US2017/039214 on Jun. 26, 2017, now Pat. No. 10,769,786.

(60) Provisional application No. 62/355,780, filed on Jun. 28, 2016.

(51) Int. Cl.
| | |
|---|---|
| *G06T 7/149* | (2017.01) |
| *G06T 7/00* | (2017.01) |
| *G06T 7/12* | (2017.01) |
| *G06T 7/11* | (2017.01) |
| *G16H 30/40* | (2018.01) |
| *A61B 5/00* | (2006.01) |
| *G16H 30/20* | (2018.01) |

(52) U.S. Cl.
CPC .......... *G06T 7/0012* (2013.01); *A61B 5/0013* (2013.01); *A61B 5/0077* (2013.01); *A61B 5/445* (2013.01); *A61B 5/7475* (2013.01); *G06T 7/11* (2017.01); *G06T 7/12* (2017.01); *G06T 7/149* (2017.01); *G16H 30/20* (2018.01); *G16H 30/40* (2018.01); *G06T 2207/20104* (2013.01); *G06T 2207/20116* (2013.01); *G06T 2207/30088* (2013.01)

(58) Field of Classification Search
CPC . G06T 7/0012; G06T 7/10; G06T 7/11; G06T 7/12; G06T 7/149; G06T 7/194; G06T 2207/20104; G06T 2207/20116; G06T 2207/30088; G16H 30/40; A61B 5/0077; A61B 5/445; A61B 5/7271; A61B 5/7275
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Esher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

International Search Report and Written Opinion, Corresponding to PCT/US2017/039214, dated Dec. 13, 2017.
Zulueta-Coarasa, Teresa, "Automated multidimensional image analysis reveals a role for Abl in embryonic wound repair," Development, vol. 141, No. 14, Jul. 15, 2014, pp. 2901-2911.
Oduncu et al., "Analysis of Skin Wound Images Using Digital Color Image Processing: A Preliminary Communication", Lower Extremity Wounds, vol. 3, No. 3, 2004, pp. 151-156. (Year: 2004).
Fernandez-Gonzalez et al., "Oscillatory behaviors and hierarchical assembly of contractile structures in intercalating cells", Physical Biology, vol. 8, Aug. 2011, p. 045005. (Year: 2011).

(Continued)

*Primary Examiner* — Andrew W Johns

(57) ABSTRACT

In one example embodiment, a wound imaging system includes a user interface, a computer processor, and an active contouring module. The user interface is configured to display an image of a wound acquired by the wound imaging system and selectively receive inputs from a user defining an initial perimeter of the wound. An active contouring module is configured to operate on the computer processor to receive the inputs defining the initial perimeter of the wound, identify features of the image on opposing sides of the initial perimeter of the wound, and identify an actual perimeter of the wound based on the initial perimeter of the wound and the identified features. The user interface is further configured to display, on the image of the wound, the actual perimeter of the wound as identified by the active contouring module and selectively receive inputs from the user to modify the actual perimeter of the wound.

20 Claims, 25 Drawing Sheets

(56) References Cited

U.S. PATENT DOCUMENTS

| | | |
|---|---|---|
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Wall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 10,013,527 B2 | 7/2018 | Fairbairn et al. |
| 10,769,786 B2 | 9/2020 | Moore |
| 11,315,245 B2 * | 4/2022 | Moore .................. G16H 30/20 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0213213 A1 | 8/2009 | Fright et al. |
| 2010/0091104 A1 | 4/2010 | Sprigle et al. |
| 2014/0163491 A1 | 6/2014 | Schuessler et al. |
| 2015/0080788 A1 | 3/2015 | Blott et al. |
| 2015/0150457 A1 | 6/2015 | Wu et al. |
| 2016/0284084 A1 | 9/2016 | Gurcan et al. |
| 2017/0076446 A1 | 3/2017 | Pedersen et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Hettiarachchi et al., "Mobile Based Wound Measurement", IEEE Point-of-Care Healthcare Technologies (PHT), Jan. 2013, pp. 298-301. (Year: 2013).

Active Contour Model; Webpage; Wikipedia, updated Oct. 2, 2019 [retrieved Dec. 9, 2019]; Retrieved from the Internet: <https://en.wikipedia.org/wiki/Active_contour_model>.

Philippe Andrey and Thomas Boudier; "Adaptive Active Contours (Snakes) for the Segmentation of Complex Structures in Biological Images"; 2007; 1-5.

(56) References Cited

OTHER PUBLICATIONS

Laurent D. Cohen; "On Active Contour Models"; RR-1075, INRIA; 1989.
Lee C. Rogers, et al.; "Digital Planimetry Results in More Accurate Wound Measurements: A Comparison to Standard Ruler Measurements"; Jul. 2010; 799-802; Journal of Diabetes Science and Technology; vol. 4, Issue 4.
Marina Kolesnik and Alex Fexa; "Multi-dimensional Color Histograms for Segmentation of Wounds in Images"; Image Analysis and Recognition; 2005; 1014-1022; Springer, Berlin, Heidelberg.
Begoña Acha, et al.; "Segmentation and Classification of Burn Color Images"; Papers from 23rd Annual International Conference of the IEEE Engineering in Medicine and Biology Society; Oct. 25, 2001.
Mohammad Faizal Ahmad Fauzi, et al.; "Segmentation and Automated Measurement of Chronic Wound Images: Probability Map Approach"; SPIE Proceedings; Mar. 24, 2014; 8; vol. 9035; SPIE.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoviƒ, V. ?ukiƒ, Ž. Maksimoviƒ, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 653-562 (Morykwas I).
C.E. Tennants, "The Use of Hypermia in the Postoperative Treatment of Lesions of the Extremities and Thorax, " Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C. @ Therapy Clinical Guidelines: A Reference Source for Clinicians; Jul. 2007.

* cited by examiner

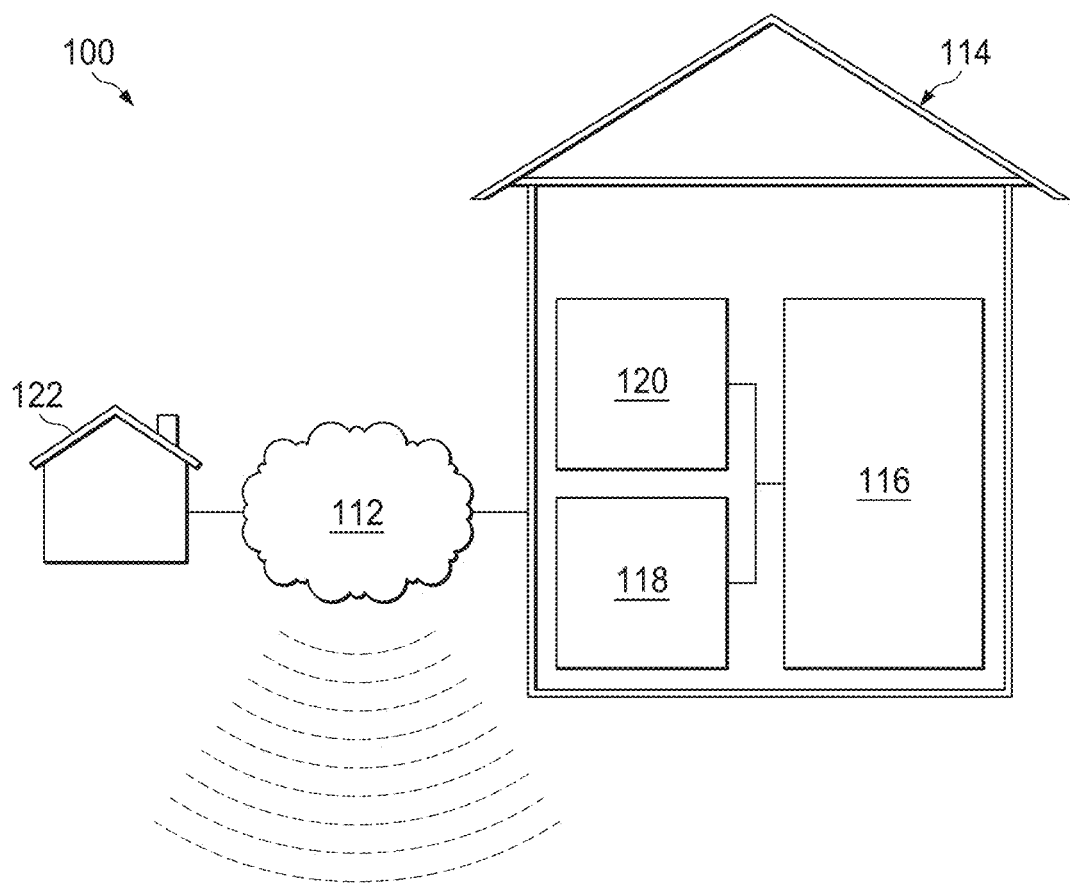
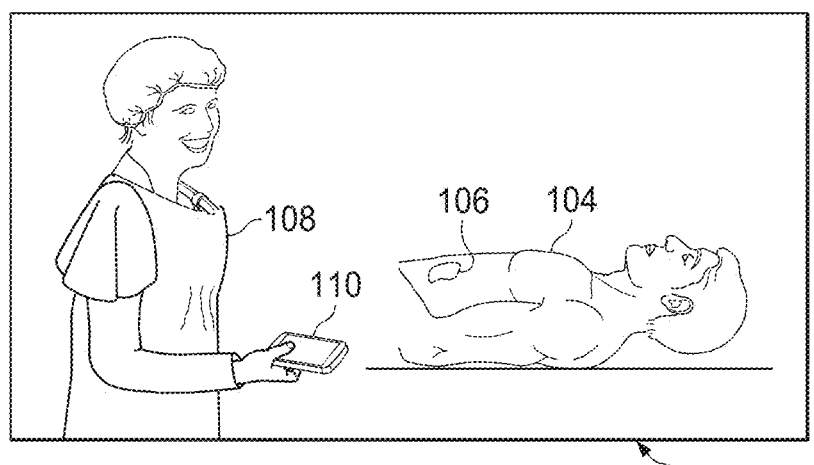
FIG. 1

| | |
|---|---|
| Patient | XXXXX XXXX |

Wound Information

Anatomical Location
Foot - Dorsal - Left

Wound Etiology
Ulcer

Tissue Damage
Full Thickness  >

Exposed Structures
Bones, Subcutaneous Tissue

Wound Images (2)
☐ ☐

💬 Add a Message  >

Wound Dimensions (cm)
20.00 x 30.00 x 8.00

Other Wound Conditions
Tunneling

Exudate (Amount-Appearance)
Moderate (Moist)

FIG. 2

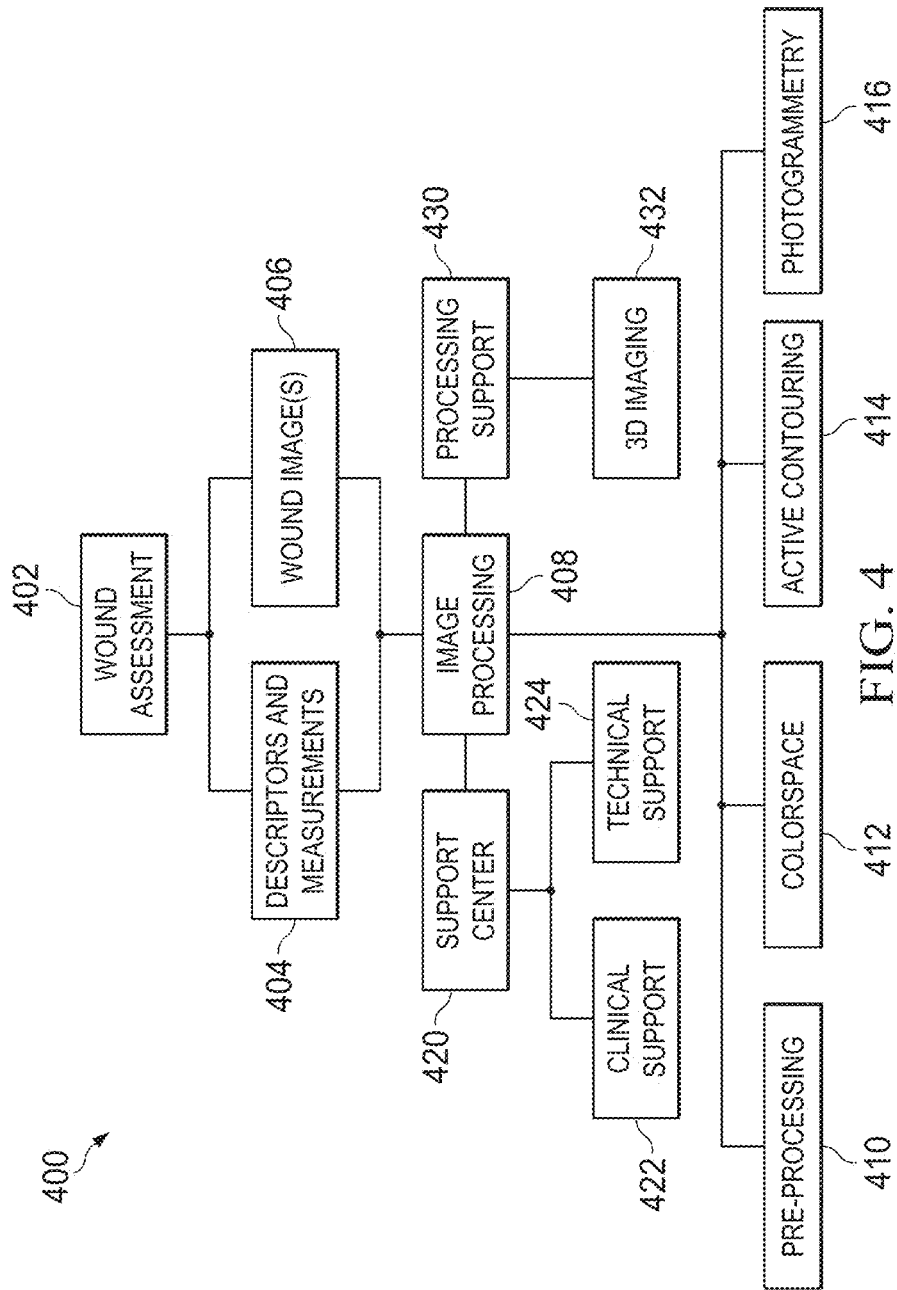

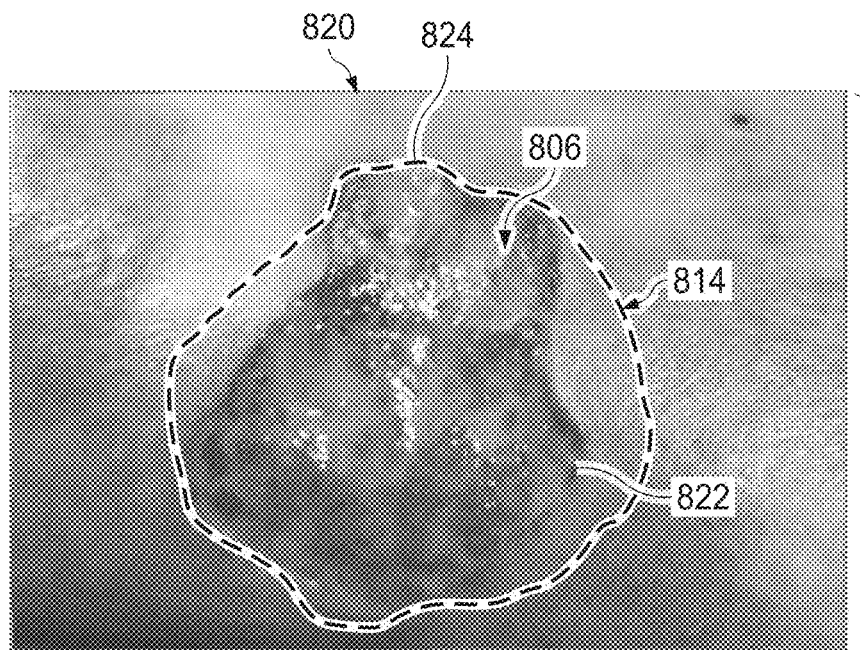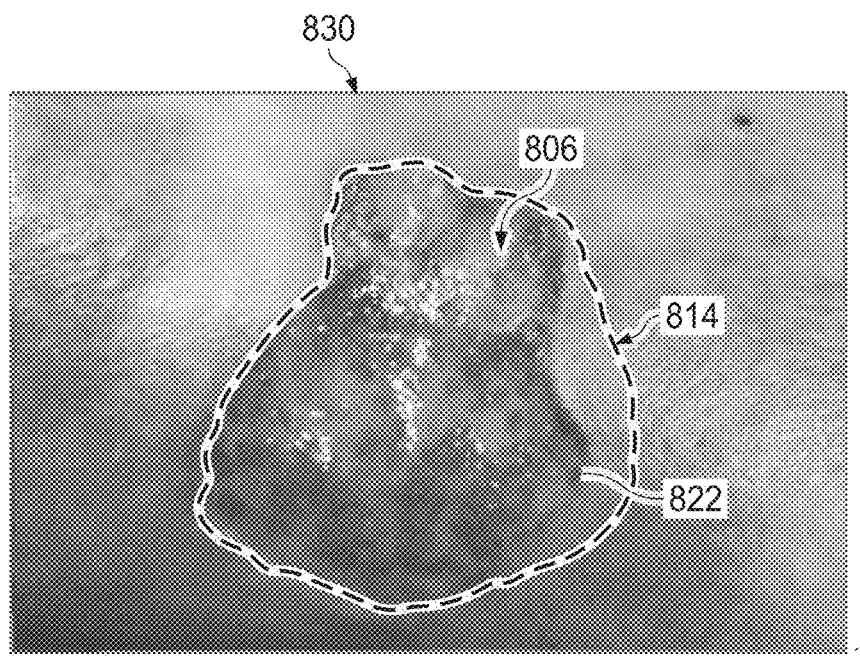
FIG. 8B

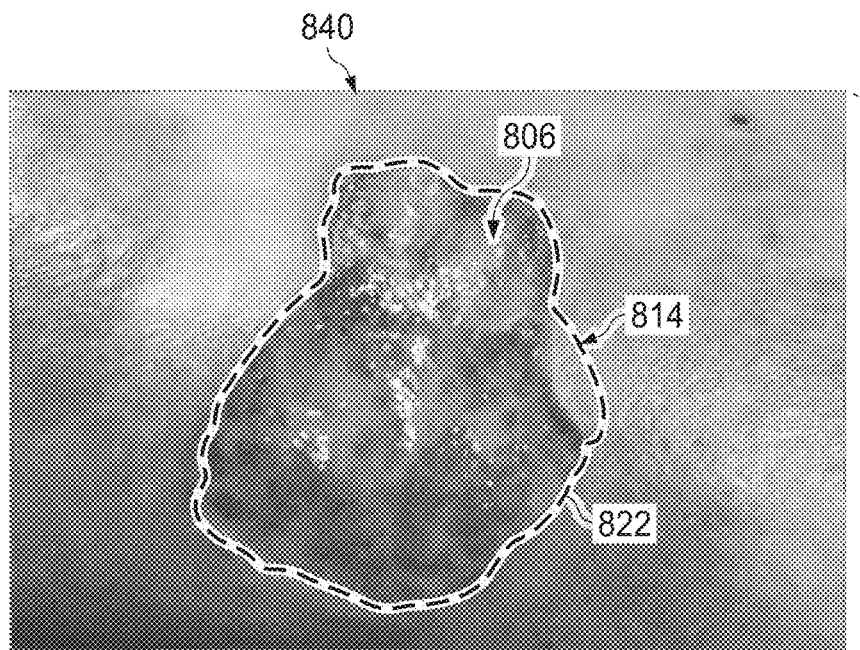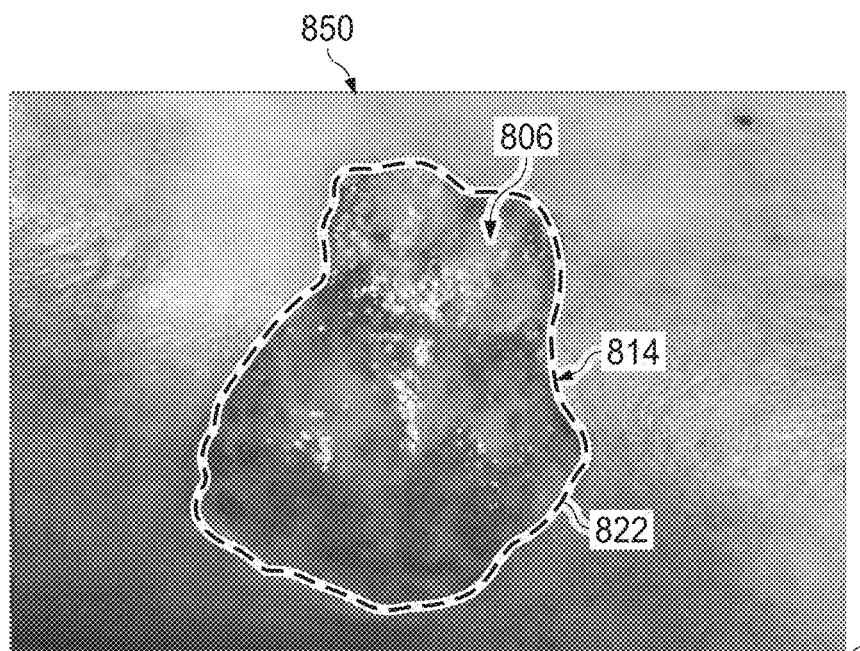
FIG. 8C

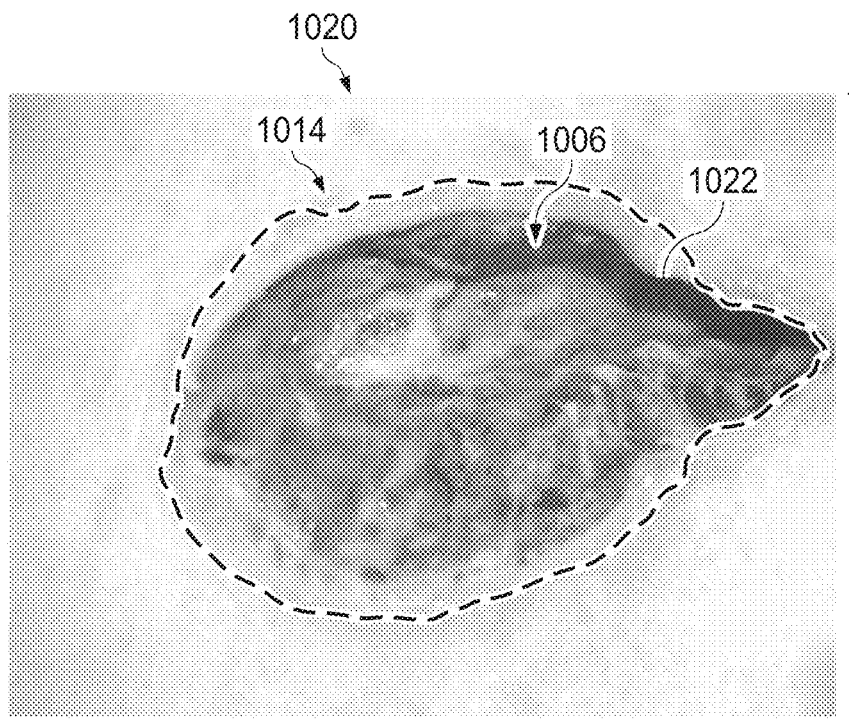
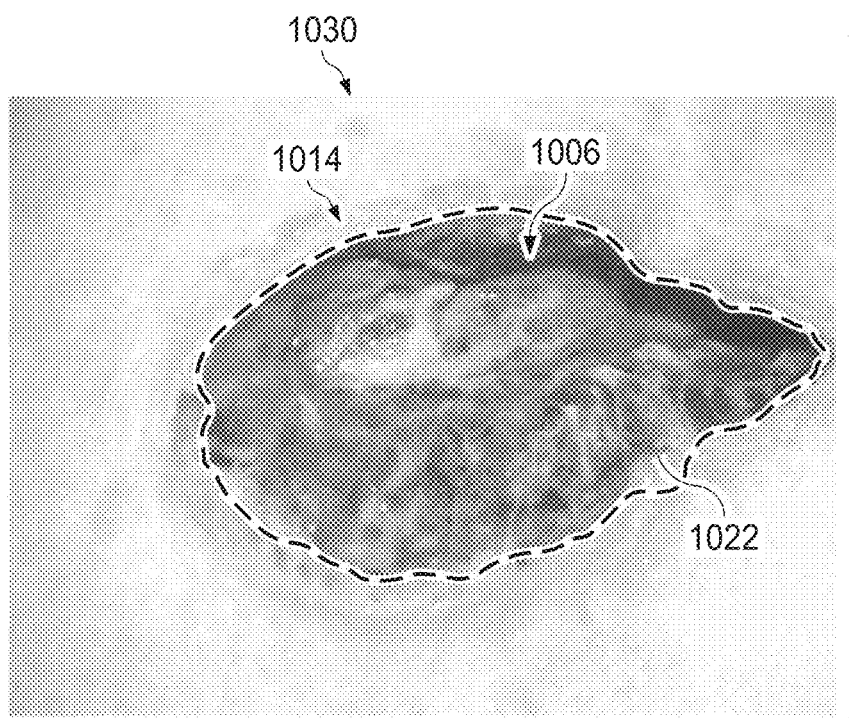
FIG. 10B

SEMI-AUTOMATED SYSTEM FOR REAL-TIME WOUND IMAGE SEGMENTATION AND PHOTOGRAMMETRY ON A MOBILE PLATFORM

RELATED APPLICATIONS

This application is a Continuation of U.S. patent application Ser. No. 16/986,878, entitled "SEMI-AUTOMATED SYSTEM FOR REAL-TIME WOUND IMAGE SEGMENTATION AND PHOTOGRAMMETRY ON A MOBILE PLATFORM", filed Aug. 6, 2020, which is a Continuation of U.S. patent application Ser. No. 16/308,158, entitled "SEMI-AUTOMATED SYSTEM FOR REAL-TIME WOUND IMAGE SEGMENTATION AND PHOTOGRAMMETRY ON A MOBILE PLATFORM", filed Dec. 7, 2018, which is a National Stage application claiming priority to PCT Application No. PCT/US2017/039214, entitled "SEMI-AUTOMATED SYSTEM FOR REAL-TIME WOUND IMAGE SEGMENTATION AND PHOTOGRAMMETRY ON A MOBILE PLATFORM", filed Jun. 26, 2017, which claims the benefit, under 35 USC 119(e), of the filing of U.S. Provisional Patent Application No. 62/355,780, entitled "SEMI-AUTOMATED SYSTEM FOR REAL-TIME WOUND IMAGE SEGMENTATION AND PHOTOGRAMMETRY ON A MOBILE PLATFORM," filed Jun. 28, 2016, which are incorporated herein by reference for all purposes.

TECHNICAL FIELD

The invention set forth in the appended claims relates generally to tissue treatment systems. More particularly, but without limitation, the present disclosure relates to systems and methods for accomplishing acquisition and processing of wound images, as well as photogrammetry.

BACKGROUND

A wound is generally defined as a break in the epithelial integrity of the skin. Such an injury, however, may be much deeper, including the dermis, subcutaneous tissue, fascia, muscle, and even bone. Proper wound healing is a highly complex, dynamic, and coordinated series of steps leading to tissue repair. Acute wound healing is a dynamic process involving both resident and migratory cell populations acting in a coordinated manner within the extra-cellular matrix environment to repair the injured tissues. Some wounds fail to heal in this manner (for a variety of reasons) and may be referred to as chronic wounds.

Following tissue injury, the coordinated healing of a wound will typically involve four overlapping but well-defined phases: hemostasis, inflammation, proliferation, and remodeling. Hemostasis involves the first steps in wound response and repair which are bleeding, coagulation, and platelet and complement activation. Inflammation peaks near the end of the first day. Cell proliferation occurs over the next 7-30 days and involves the time period over which wound area measurements may be of most benefit. During this time, fibroplasia, angiogenesis, re-epithelialization, and extra-cellular matrix synthesis occur. The initial collagen formation in a wound typically peaks in approximately 7 days. The wound re-epithelialization occurs in about 48 hours under optimal conditions, at which time the wound may be completely sealed. A healing wound may have 15% to 20% of full tensile strength at 3 weeks and 60% of full strength at 4 months. After the first month, a degradation and remodeling stage begins, wherein cellularity and vascularity decrease and tensile strength increases. Formation of a mature scar often requires 6 to 12 months.

There are various wound parameters that may assist a clinician in determining and tracking healing progress of a wound. For example, wound dimensions, including wound area and volume measurements, may provide a clinician with knowledge as to whether or not a wound is healing and, if the wound is healing, how rapidly the wound is healing. Wound assessment is an important process to properly treating a wound, as improper or incomplete assessment may result in a wide variety of complications.

While wound measurements may provide valuable parameters for helping a clinician assess wound healing progress, the size of the wound may not provide a clinician with a full picture to fully assess whether or how a wound is healing. For example, while the size of a wound may be reduced during treatment, certain parts of a wound may become infected. A clinician may often-times examine wound tissue for its color and texture to determine how a wound is healing. Wound tissue includes a wound bed and peri-wound areas or wound edges. Health of a wound may be determined by color of tissue, with certain problems often presenting with distinct colors at the wound. For example, normal granulation tissue typically has a red, shiny textured appearance and bleeds readily, whereas necrotic tissue (i.e., dead tissue) may either be yellow-gray and soft, generally known as "slough" tissue, or hard and blackish-brown in color, generally known as "eschar" tissue. A clinician may observe and monitor these and other wound tissues to determine wound healing progress of the overall wound, as well as specific wound regions.

Because wound treatment can be costly in both materials and professional care time, a treatment that is based on an accurate assessment of the wound and the wound healing process can be essential.

SUMMARY

New and useful systems, apparatuses, and methods for wound image segmentation are set forth in the appended claims. Illustrative embodiments are also provided to enable a person skilled in the art to make and use the claimed subject matter.

For example, in some embodiments, systems and methods according to the principles of the present disclosure provide user-assisted wound perimeter identification implementing active contouring. A touchscreen is provided for allowing a user to establish an initial, rough outline around a perimeter of a wound in an acquired image displayed on the touchscreen. An active contour process is then applied to the image using the initial outline provided by the user to accurately identify the actual wound perimeter for further image processing.

In some embodiments, a wound imaging system may include a non-transitory computer readable medium for storing a wound image, a computer processor, and an active contouring module. The computer processor may be configured to output for display the wound image, as well as selectively receive via a user interface a first input from a user defining an initial perimeter of a wound displayed in the wound image. The computer processor may be further configured to execute an active contouring module configured to identify features of the wound image on opposing sides of the initial perimeter of the wound and to identify an actual perimeter of the wound based on the first input and the identified features. The computer processor may also be further configured to output for display a graphical representation of the identified actual perimeter of the wound. Additionally, the computer processor may be further configured to receive a second input from the user to modify or confirm the actual perimeter of the wound.

Alternatively, other example embodiments may implement a wound imaging method that includes displaying a wound image stored on a non-transitory computer readable medium, selectively receiving a first input from a user defining an initial perimeter of a wound displayed in the wound image, executing, by a computer processor, an active contouring module configured to identify features of the wound image on opposing sides of the initial perimeter of the wound, determining, by the computer processor, an actual perimeter of the wound displayed in the wound image based on the initial perimeter of the wound and the identified features, outputting for display, by the computer processor, a graphical representation of the determined actual perimeter of the wound as identified by the active contouring module, and selectively receiving, by the computer processor, a second input from the user to modify the actual perimeter of the wound.

In an example embodiment, a wound imaging system may include a computer processor and an active contouring module configured to be executed by the computer processor. The computer processor may be configured to output for display on a touchscreen an image of a wound acquired by the wound imaging system, process a first input from a user on the touchscreen defining an initial perimeter of the wound, the first input including a plurality of points establishing a polygon around the wound, and process a second input from the user on the touchscreen indicating that the user has completed defining the initial perimeter. The active contouring module may be configured to receive the first input defining the initial perimeter of the wound and the second input indicating that the user has completed defining the initial perimeter, generate an initial active contour corresponding to the initial perimeter, identify features of the image on opposing sides of the initial active contour, and, based on the identified features, iteratively modify the initial active contour to calculate a final active contour corresponding to an actual perimeter of the wound. The touchscreen may be further configured to display the final active contour calculated by the active contouring module Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 1 is an illustration of a therapy network in accordance with an exemplary embodiment;

FIG. 2 is an illustration of a screen shot of a graphical user interface (GUI) of a mobile wound imaging software for operation on an electronic device, in accordance with the exemplary embodiment of FIG. 1;

FIG. 4 illustrates a functional diagram of a wound imaging software according to an exemplary embodiment that may be associated with some example embodiments of the therapy network according to FIG. 1;

FIGS. 8A-8D illustrate example views associated with an exemplary image processing method in accordance with the specification for an example wound image;

FIGS. 10A-10C illustrate example views associated with an exemplary image processing method in accordance with the specification for an example wound image;

DETAILED DESCRIPTION

Figure 3A:
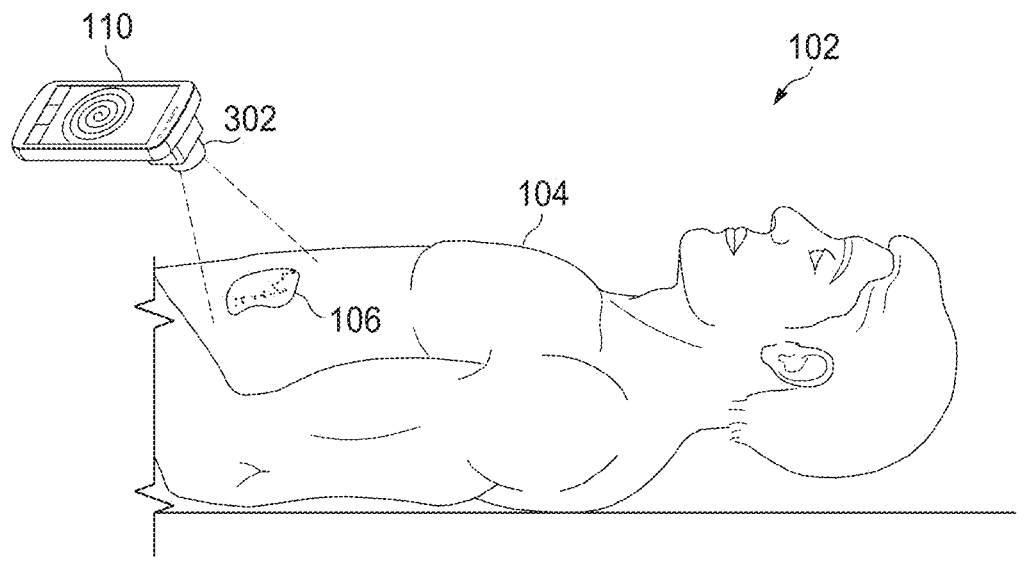
FIG. 3A is a perspective view illustrating additional details that may be associated with some example embodiments of the therapy network of FIG. 1.

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

FIG. 1 is a schematic diagram of an example embodiment of a therapy network 100 that can support a wound imaging and diagnostic application in accordance with this specification. The therapy network 100 may include a clinical setting 102, which may include an environment where a patient 104 with a tissue site 106 may be evaluated and/or treated by a clinician 108. The clinician 108 may use a mobile device 110, in conjunction with the wound imaging and diagnostic application, to capture, edit, and analyze images related to the tissue site 106.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue.

The term "clinician" is used herein as meaning any medical professional, user, family member of a patient, or patient who interacts or interfaces with the various aspects of care related to a tissue site.

A mobile device for the purposes of this application may be any combination of a computer or microprocessor. The computer or microprocessor may be programmed to implement one or more software algorithms for achieving the functionality described in the specification and corresponding figures. The mobile device, such as mobile device 110, may also include a communication device, and may be a smartphone, a tablet computer, or other device that is capable of storing a software application programmed for a specific operating system (e.g., iOS, Android, and Windows). The mobile device 110 may also include an electronic display, such as a graphical user interface (GUI), for providing visual images to a user, such as a clinician or patient. The mobile device 110 may be configured to communicate with one or more networks 112 of the therapy network 100. In one preferred embodiment, the mobile device 110 may include a cellular modem and may be configured to communicate with the network(s) 112 through a cellular connection. In other embodiments, the mobile device 110 may include a Bluetooth® radio or other wireless radio technology for communicating with the network(s) 112. The mobile device 110 may be configured to transmit data related to the tissue site 106 of the patient 104.

The therapy network 100 may also include a support center 114 that may be in communication with the mobile device 110 through network(s) 112. For example, the mobile device 110 may be configured to transmit data through network(s) 112 to the support center 114. The support center 114 may support a wound imaging database 116. In some embodiments, the support center 114 may include both a clinical support center 118 and a technical support center 120. The clinical support center 118 may function as a centralized center for clinicians to contact regarding questions they may have related to imaging of specific wounds with which they may be presented. The technical support center 120 may serve as a contact point for solving technical issues with use of the wound imaging and diagnostic application.

The therapy network 100 may also include other entities that may communicate with clinical settings, mobile devices, and support centers through network(s) 112. For example, the therapy network 100 may include a third party 122. In some embodiments, the third party 122 may be an image-processing vendor. Various image-processing vendors may be included as part of the therapy network 100, to provide expertise and support for wound images that may be particularly unique or challenging to process and analyze. Such image-processing vendors may offer one or more additional software packages that may be used for processing specific aspects of captured wound images. In these embodiments, a representative in the clinical support center 118 may determine that a particular image requires the additional processing expertise offered by a specific image-processing vendor and may route the image file(s) to that vendor. In some embodiments, the wound imaging and diagnostic application may prompt the user, such as the clinician, for routing the image to the third-party vendor, or in some cases, may be configured to automatically route the image to one or more particular image-processing vendors.

Referring to FIG. 2, a screen shot of an illustrative graphical user interface (GUI) 200 of an exemplary embodiment of the wound imaging and diagnostic application is shown. As already discussed, the wound imaging and diagnostic application may operate on a mobile device, such as a smartphone. Following logging into the wound imaging and diagnostic application, a user, such as a clinician, may be presented with a menu bar 202, which in some embodiments may be located across the bottom of the GUI 200. The menu bar 202 of the GUI 200 may include a number of selectable graphical elements, including a "Your Patients" soft-button 204, "Image Library" soft-button 206, "Search" soft-button 208, "Contact Us" soft-button 210, "Sign Out" soft-button 212, along with soft-buttons assigned to any other features related to the collection, processing, and management of wound images. The user may select any of these functions (i.e., your patients, image library, search, contact us, sign out) to cause another GUI for performing the selected function to be presented to the user. For example, the "Your Patients" soft-button 204 may function to display a list of the patients assigned to the caseload of the particular user, while the "Image Library" soft-button 206 may display a list of wound images captured or reviewed by the user. The "Search" soft-button 208 may allow a user to find images or image information with respect to a given patient. Additionally, the "Contact Us" soft-button 210 may allow a user to send questions, comments, or suggestions about the wound imaging and diagnostic application to a team at the clinical support center 118 and/or the technical support center 120. The "Sign Out" soft-button 212 may allow a user to securely log out of the wound imaging and diagnostic application. It should be understood that GUI 200 is exemplary and that other and/or alternative functions and selection elements may be provided to the user.

Still referring to the exemplary screen shot of FIG. 2, an exemplary illustration of the functionality of the wound imaging and diagnostic application is shown. For example, FIG. 2 illustrates an example embodiment of a patient information view 213. The patient information view 213 may include a patient identification ribbon 214, present at the top of the patient information view 213 of the GUI 200. The patient identification ribbon 214 may provide secure information regarding one or more data items related to identifying the patient. For example, the patient identification ribbon 214 may display one or more of a patient's name, social security number, or a unique patient identification number.

In some embodiments, the patient information view 213 may include a wound information view 216. The wound information view 216 may include data fields for descriptors related to one or more wounds of a patient. For example, an anatomical location field 218 may provide a field for a descriptive location on the body of the patient where the wound is located. A wound etiology field 220 may provide a field for entering and displaying the type of wound. For example, the wound etiology field 220 may indicate that the wound is a burn, surgical wound, ulcer, or other type of wound. The wound information view 216 may also include additional descriptive fields related to the physical nature of the wound, such as a tissue damage field 222 and an exposed structures field 224. The tissue damage field 222 may allow for a description of how many layers of skin tissue are damaged, or in other words, the depth of the wound. The exposed structures field 224 may provide a space for listing any nearby structures at the tissue site that are exposed or otherwise possibly affected by the wound. A wound images field 226 may be included for displaying a collection of images of the wound. The wound images field 226 may allow for a user to tap on a particular image for a full-screen view, and may also allow the user to spread and enlarge the image for a more detailed view of particular wound aspects. The wound images displayed in the wound images field 226 may be images taken by a number of individuals, including one or more clinicians and the patient. Some embodiments of the wound images field 226 of the wound information view 216 may include functionality for transmitting the images through the image processing application. A message field 228 may allow for users to send and receive secure text and picture messages using the wound imaging and diagnostic application through the network(s) 112. For example, messages may be sent by the clinician 108 from the mobile device 110 through the network(s) 112 to the support center 114.

The wound information view 216 of the patient information view 213 may include a wound dimensions field 230, which may allow for dimensions of the wound to be entered, including length, width, and depth of the wound. The wound dimensions may be either manually entered into the wound dimensions field 230, or alternatively may be automatically determined by the wound imaging and diagnostic application based on image processing analysis of one or more images of the specific wound. The wound information view 216 may also include an other wound conditions field 232, which may be used to note any other physical characteristics or complications associated with the particular wound site. An exudate field 234 may also be included in the wound information view 216, which may be used for documenting moisture conditions at the wound site, including a classification of the amount of exudate originating from the wound. Additionally, the wound information view 216 may also include additional or alternative data fields, based on clinical applications and needs.

Referring to FIG. 3A, an exemplary patient environment, such as clinical setting 102, is shown with the patient 104 having a tissue site 106. Mobile device 110 is also shown, with an image capture device 302, which may be utilized to capture an image of the tissue site 106. The captured image may then be transmitted from the image capture device 302 to the mobile device 110. The image capture device 302 may be a digital camera, mobile telephone, or any other electronic device configured to capture an image in a digital or analog format. In general, to expedite capturing and working with an image of the tissue site 106, the image capture device 302 may be in the form of a digital camera that is configured to be physically connected to the mobile device 110 and may communicate with the mobile device 110 using a wired connection. Alternatively or additionally, the image capture device 302 may be configured to be wirelessly connected to the mobile device 110. In some embodiments, the image capture device 302 may utilize a memory device (not shown) that may be transferred between electronic devices. The memory device may include flash memory, a memory stick, or any other memory device with which the mobile device 110 may be compatible.

As previously discussed, the image capture device 302 may be used to capture images which may be incorporated into the wound imaging and diagnostic application. The captured images may then be shared among interested parties, such as the clinician, image processing vendors, and the patient. Wound images captured by the image capture device 302 may be used by the wound imaging and diagnostic application to determine and subsequently populate one or more wound dimension fields, as discussed with respect to FIG. 2. As also previously mentioned, the image capture device 302 may be a three-dimensional camera connected to the mobile device 110, which may also be used to capture wound images that may be used by the wound imaging and diagnostic application to automatically determine one or more wound dimensions and upload the dimensions to the proper data fields in the wound imaging application. Additionally, the image capture device 302 may be used to capture images of the tissue site 106 over time, in order for a clinician, a patient, or other interested party to monitor the healing progress of the tissue site 106. Users, such as clinicians, may also have the ability to upload images previously taken, which may be stored in a secure gallery on the mobile device 110. Tissue site images captured by the image capture device 302 may each be stored in an image database, such as wound imaging database 116, associated with the wound imaging and diagnostic application and therapy network 100.

Figure 3B:
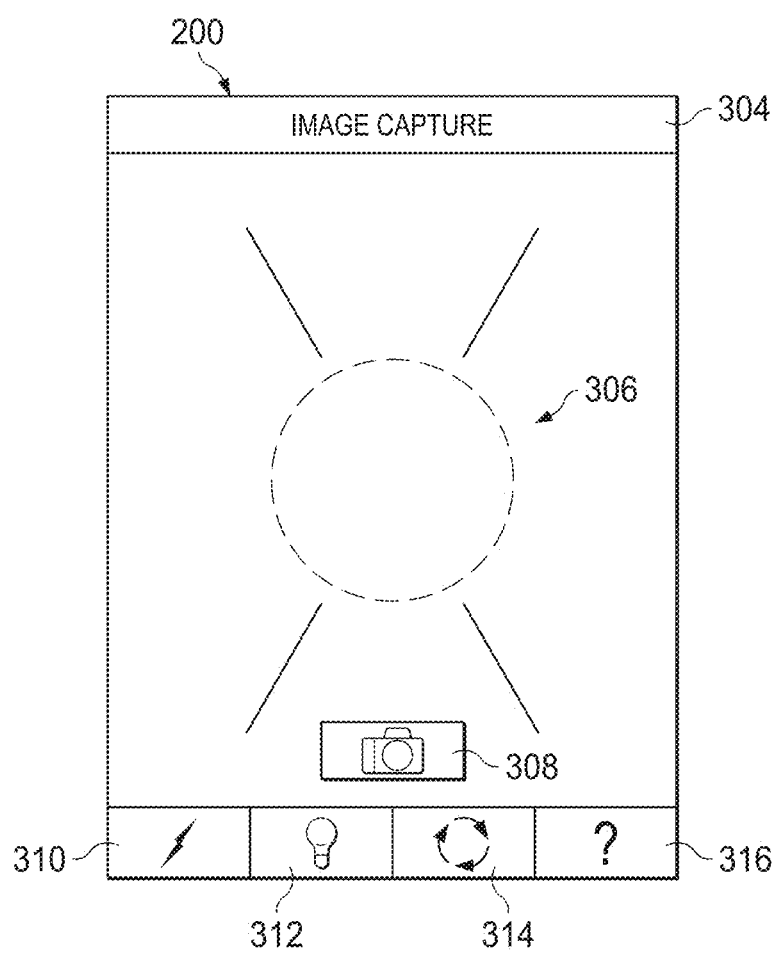
FIG. 3B illustrates a screen shot of a graphical user interface (GUI) of a mobile wound imaging software for operation on an electronic device that may be associated with some example embodiments of the therapy network according to FIG. 1.

FIG. 3B illustrates an example embodiment of an image capture view 304 of the GUI 200. In this example embodiment, the image capture view 304 and an associated image capture software module of the wound imaging and diagnostic application may provide a host of tools for aiding a user in obtaining high-quality wound images. For example, the image capture view 304 may provide the user with one or more interfaces for guiding the user with optimal camera orientation and placement during wound image capture. In some embodiments, the image capture view 304 may include targeting elements 306 to aid in focusing on a centered, full-frame image before using the image capture soft-button 308 to obtain and store the image. Additionally, the image capture software module may provide the user with a variety of image capture tools as part of the image capture view 304. For example, the image capture view 304 may include a flash soft-button 310, which may provide the user with a variety of different light and/or flash options. A light analysis soft-button 312 may also be included, which may perform an automated ambient light assessment and may potentially alert the user of the need for supplemental lighting or flash for capturing an ideal image of the wound. The image capture view 304 may also present the user with a processing soft-button 314, which may be selected to perform basic image pre-processing steps (histogram equalization, white balance assessment, etc.), for assessing the quality of a captured image. Based on this pre-processing, the imaging software may make the determination that an image should be recaptured, and may present this determination to the user as a pop-up message to the user on the image capture view 304. The image capture view 304 may also include a help soft-button 316, which may provide a user with a variety of instructions as well as options for contacting a support center for further assistance.

Figure 3C:
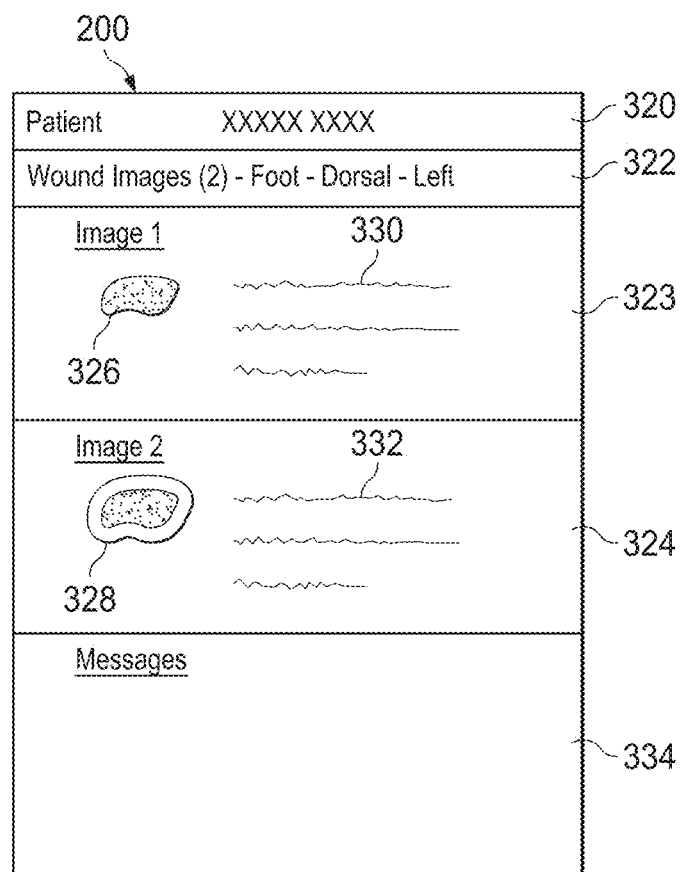
FIG. 3C is an illustration of a screen shot of a graphical user interface (GUI) of a mobile wound imaging software for operation on an electronic device that may be associated with some example embodiments of the therapy network according to FIG. 1.

FIG. 3C shows a screen shot of the illustrative GUI 200 with an example embodiment of a wound images view 320. In some embodiments, the wound images view 320 may be accessed through the wound images field 226 of the patient information view 213. The wound images view 320 may display one or more images of a single tissue site, or in some embodiments, of multiple tissue sites for a given patient. The wound images view 320 may include a tissue site identification field 322, which may indicate the location or locations of the tissue site(s) of the images displayed as part of the wound images view 320. The wound images view 320 may include a first image field 323 and a second image field 324. The first image field 323 may include a first image 326 of a single tissue site, while the second image field 324 may include a second image 328 of the same tissue site. In some embodiments, the first image field 323 and the second image field 324 may include images of different tissue sites, with the multiple tissue sites being identified in the tissue site identification field 322. By selecting the respective image of one of the image fields, a user may be presented with options for editing an image, enlarging the image for a more detailed view, drawing traces around the image, or performing other types of image modification or manipulation. In some embodiments, the image fields, such as first image field 323 and second image field 324, may include data entry fields, such as notes fields 330 and 332, for allowing the user to enter descriptions, measurements, or other information relevant to the respective image. Additionally, some embodiments of the wound images view 320 may include a messaging display 334. The messaging display 334 may allow for users to send and receive secure messages, including images, to the support center 114, to external image-processing vendors, or to other clinicians.

FIG. 4 is a functional diagram illustrating capabilities of an example embodiment of a wound imaging and diagnostic application for use on a therapy network 100. The wound imaging and diagnostic application 400 may be hosted by a secure server, which may be based on a HIPAA-compliant secure platform. The wound imaging and diagnostic application 400 may be operable on any suitable platform, including iOS, Android, and an HTML-based platform. The wound imaging and diagnostic application 400 may provide various functions depending on the particular patient and type(s) of wounds presented.

As shown in FIG. 4, the wound imaging and diagnostic application 400 may provide multiple functional modules. The wound assessment module 402 coordinates the gathering of wound images and descriptive information associated with the respective images. For example, the wound assessment module 402 may coordinate with the descriptors and measurements module 404 to provide an interface for a user to enter general patient information, as well as to collect and assess measurements and other descriptive information for one or more wounds. For example, a user, such as a clinician, may interface with multiple different views of the GUI 200 associated with the descriptors and measurements module 404 to enter dimensions and various other categories of information for the one or more wounds. The wound images module 406 may enable the user to collect one or more new images, using the associated image capture device 302 and the image capture view 304 of the GUI 200. The wound images module 406 may provide the functional interface for a user to capture, edit, and assess images of one or more wounds. In some embodiments, the wound images module 406 may also have the functionality for importing previously-taken images of one or more tissue sites, such as wounds, for the given patient.

The wound assessment module 402 and the associated descriptors and measurements module 404 and wound images module 406 may communicate with the image processing module 408. In some embodiments, the image processing module 408 may provide the user with a list of possible image processing functions that may be performed for the collected images of the one or more tissue sites. For example, the image processing module 408 may coordinate with a multitude of additional modules that include a variety of image processing capabilities. In some embodiments, the image processing module 408 may communicate with a pre-processing module 410, a color-space processing module 412, an active contouring module 414, and a photogrammetry module 416.

Additionally, the image processing module 408 may be in communication with a support center module 420, which may coordinate with a clinical support module 422 and a technical support module 424. The collective support center modules may provide a user with the option of seeking assistance with various aspects of the wound imaging and diagnostic application 400. Furthermore, the image processing module 408 may communicate with a processing support module 430. The processing support module 430 may provide active interfaces to one or more modules for communicating with external image-processing vendors, applications, etc. Example image-processing vendors and/or applications include, but are not limited to, 3D scanning/imaging application 432 for mobile devices.

Returning to the image processing module 408, a variety of core image processing features may be included. For example, once the pre-processing steps have been completed by the pre-processing module 410, the image processing module 408 may make the determination of whether the image meets initial quality thresholds. Included in the image processing module 408 may be the software for passing the image through one or more processes to elucidate key diagnostic features specific to tissue sites, and particularly wounds. In some embodiments, the image processing module 408 may coordinate with the color-space module 412. In some embodiments, the color-space module 412 may be used to first convert a standard Red-Green-Blue (RGB) image into an alternate color-space, such as Hue-Saturation-Value (HSV), Cyan-Magenta-Yellow-Black (CMYK), and/or Lab. For example only, in image detection and processing, various features may be detected more easily in different color-spaces. Some color-spaces (e.g., CMYK, Lab, etc.) may facilitate detection and processing of image features related to wound imaging. For example, skin coloration may be more easily detectable in the CMYK and Lab color-spaces. The image processing module 408 may also coordinate with an active contouring module 414, which may include software algorithms for performing a degree of low-level structural analysis of a wound image. Additionally, the image processing module 408 may communicate with a photogrammetry module 416, for providing further analysis of wound images.

Figure 5A:
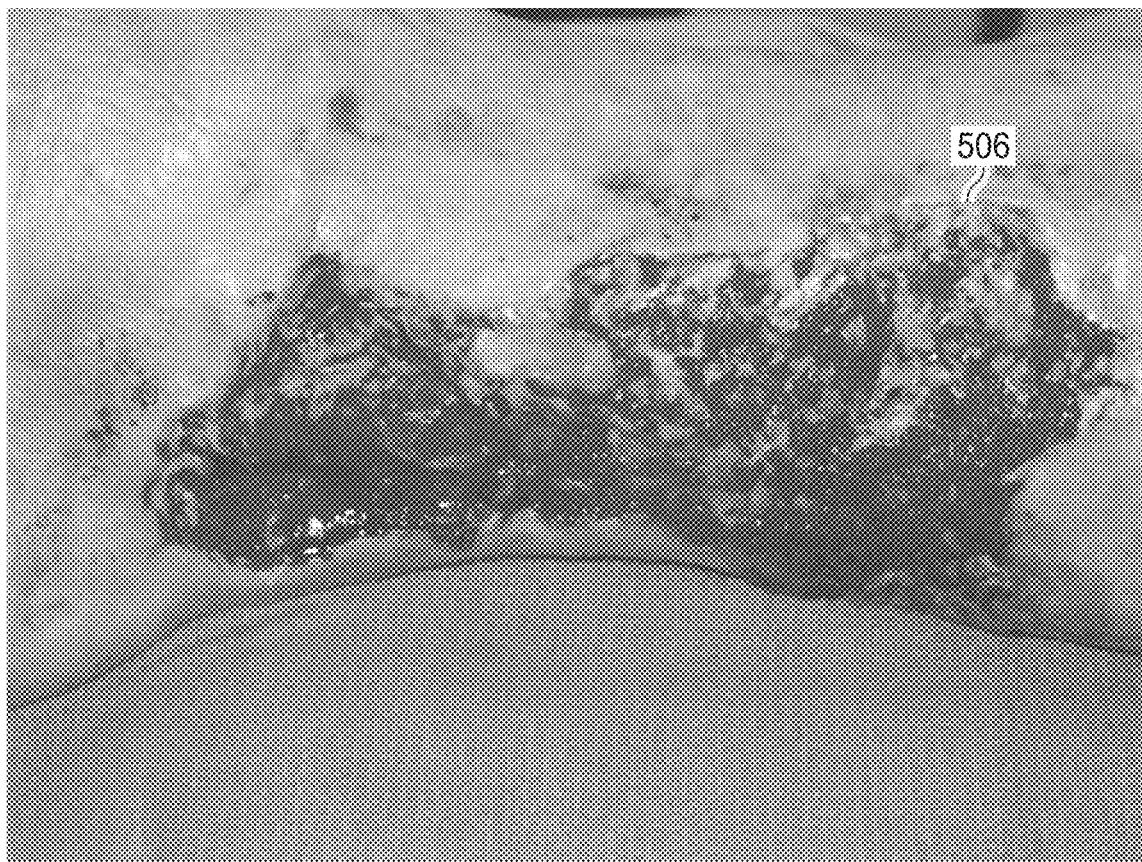
FIG. 5A illustrates an example wound image before undergoing image processing in accordance with the specification.
Figure 5B:
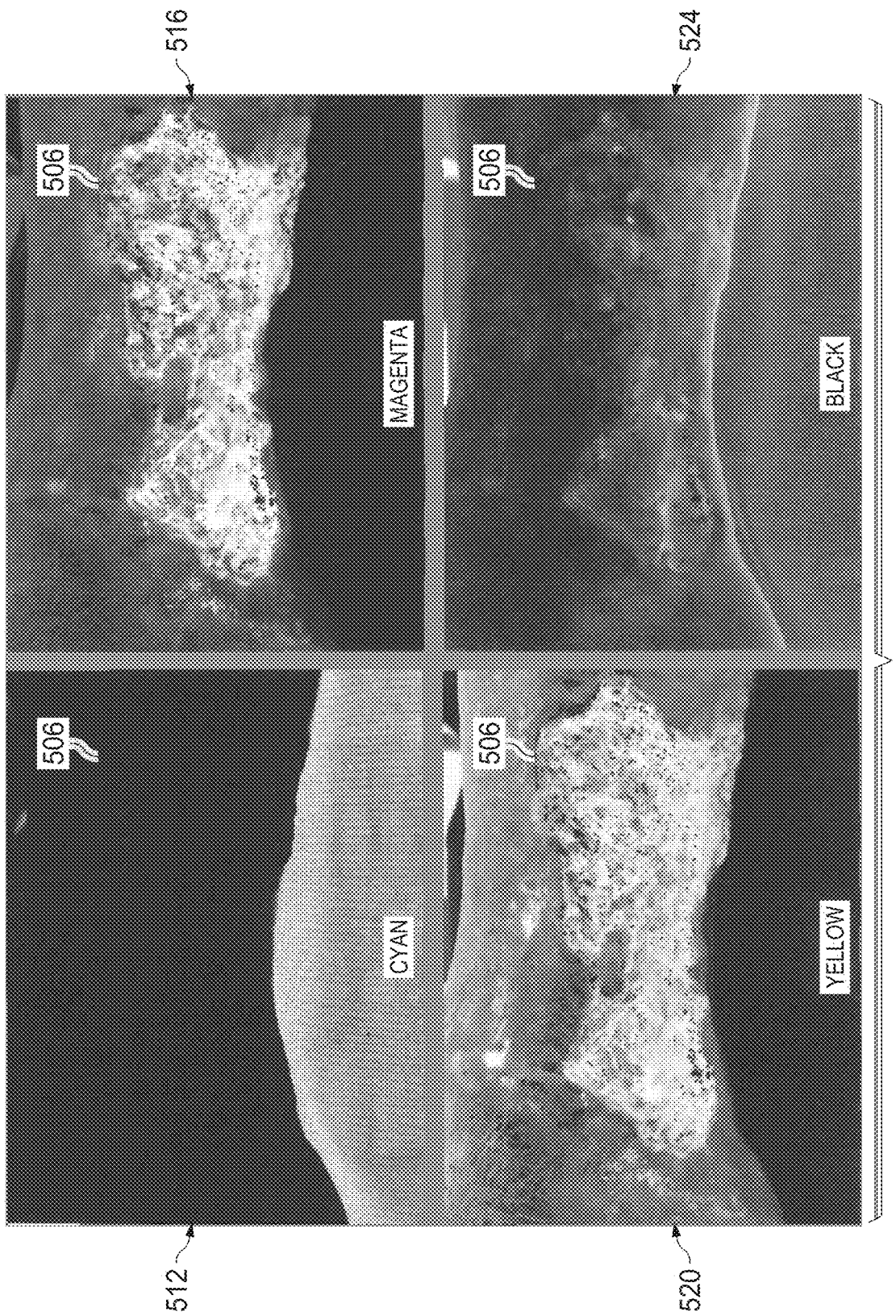
FIG. 5B illustrates example views of the wound image of FIG. 5A after undergoing processing to convert the wound image to alternative color spaces.

FIG. 5, collectively illustrates a wound image before and after conversion to the CMYK space. FIG. 5A shows a RGB image of a freshly debrided wound 506 located on the lower calf and ankle of a patient. FIG. 5B shows the imaged wound following conversion of the image to the CMYK space, illustrating the CMYK decomposition of the wound image. In such a CMYK decomposition, view 512 shows the image in the cyan space, view 516 shows features of the wound in the magenta space, view 520 highlights aspects of the wound in the yellow space, and view 524 shows the image of the wound in the black space. As shown in view 512 of FIG. 5B, the wound 506 does not contribute to the Cyan channel. On the other hand, the Magenta and Yellow channels illustrate how alternate color representations may highlight specific attributes of the appearance of the wound 506, as shown in view 516 and view 520, respectively, of FIG. 5B.

Figure 5C:
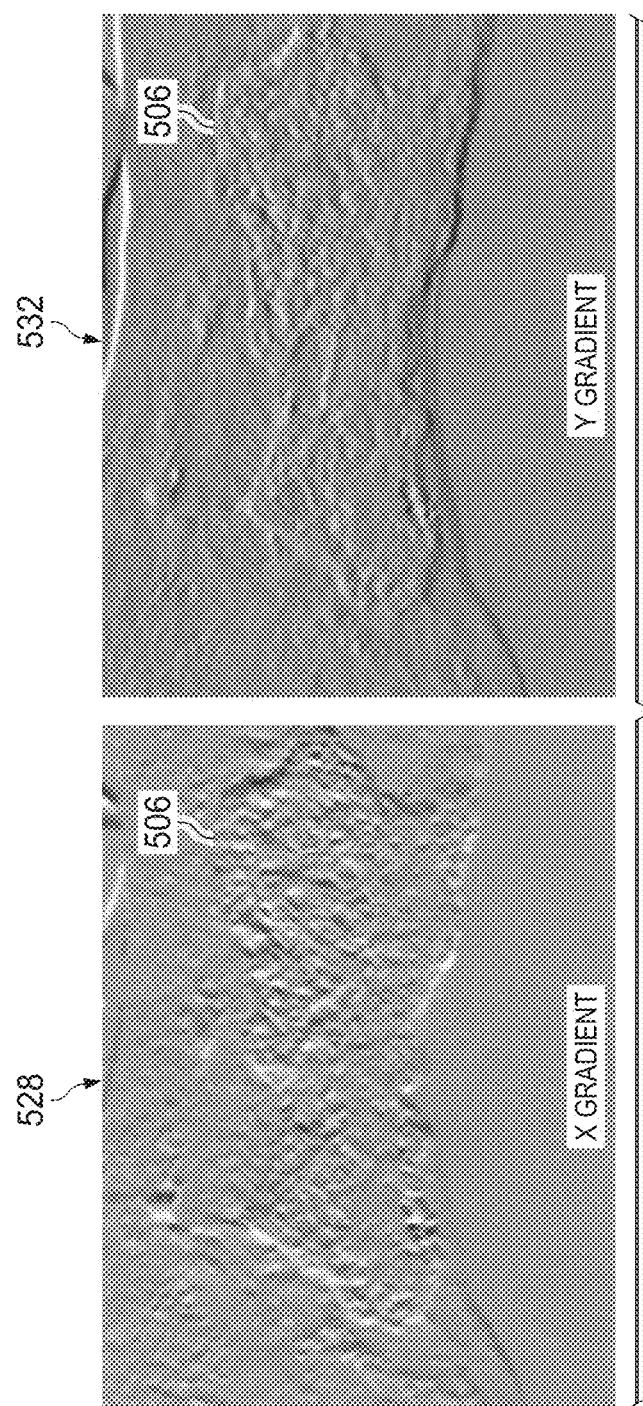
FIG. 5C illustrates example views of the wound image of FIG. 5A after undergoing processing to highlight specified gradients, in accordance with the specification.

The image processing module 408 may also include software for performing a degree of low-level structural analysis. For example, FIG. 5C illustrates views of the intensity gradient decomposition of the wound image shown in FIG. 5A. For example, view 528 illustrates the X-gradient view of the wound 506, while view 532 illustrates the Y-gradient view of the wound 506. The views of FIG. 5C also further illustrate some key characteristics of the wound 506. For example, in general, wound extents are typified by rapid, discontinuous changes in image intensity that reflect the chaotic texture of the wound bed. Image intensity generally corresponds to the brightness of pixels in the selected-color space. For example, a low intensity pixel may have low brightness (e.g., a black pixel) while a high intensity pixel may have high brightness (e.g., a white pixel). Absolute intensity may not be relevant to detection of individual features. Conversely, relative brightness (i.e., the intensity of a pixel relative to neighboring pixels) may be indicative of various features in an image. For example, relative intensity may indicate discontinuities in an image that correspond to the perimeter of a wound.

Figure 6:
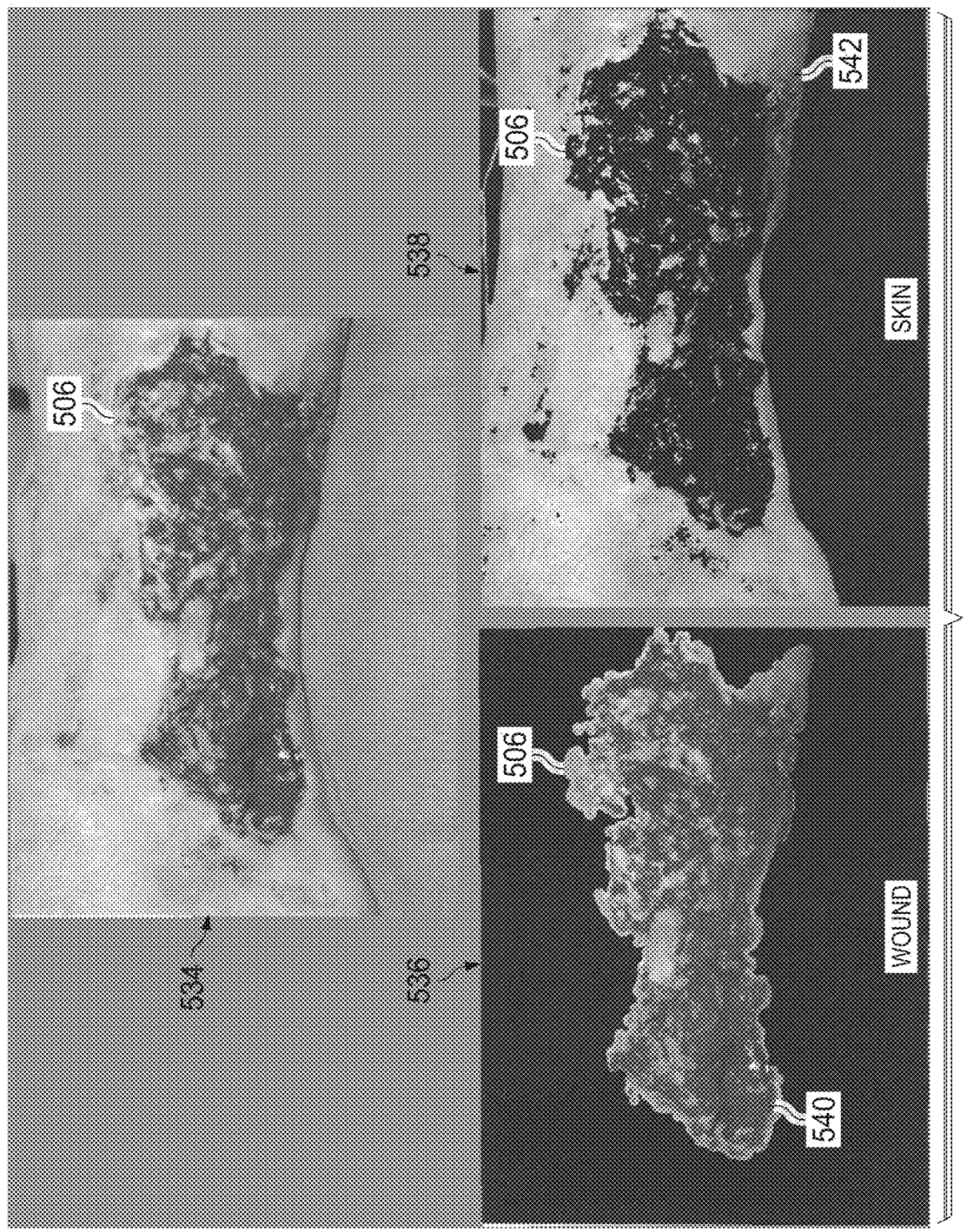
FIG. 6 illustrates example views of the result of a skin classification operator as applied to the wound image of FIG. 5A.

The image processing module 408 may also include the appropriate algorithms for applying image filters for classifying regions of images. For example, skin and wound filters may be applied in order to classify image regions as skin, wound, or not relevant, as well as any other classifications that may be applied based on how different image filters may be tailored. In one example, the filters identify (e.g., by applying/storing a label or other indicator) each pixel as a skin, wound, etc. If a first pixel is identified as "skin" but all surrounding pixels are identified as "wound," the filters may modify the identification of the first pixel from "skin" to "wound." FIG. 6 illustrates results of a skin classification filter operator, as applied to the wound image of FIG. 5A, shown again as view 534 of FIG. 6. As can be seen in FIG. 6, following the filter application and processing, two separate views can be generated from the wound image of FIG. 5A. In this illustrative example, the first view is a wound classification view 536, which highlights the portion or portions of the original wound image that were determined to be wound tissue, such as wound portion 540. In this illustrative example, the second view is a skin classification view 538, which shows the portions of the original wound image of FIG. 5A that were determined to be surrounding skin tissue, such as surrounding tissue portion 542.

Figure 7A:
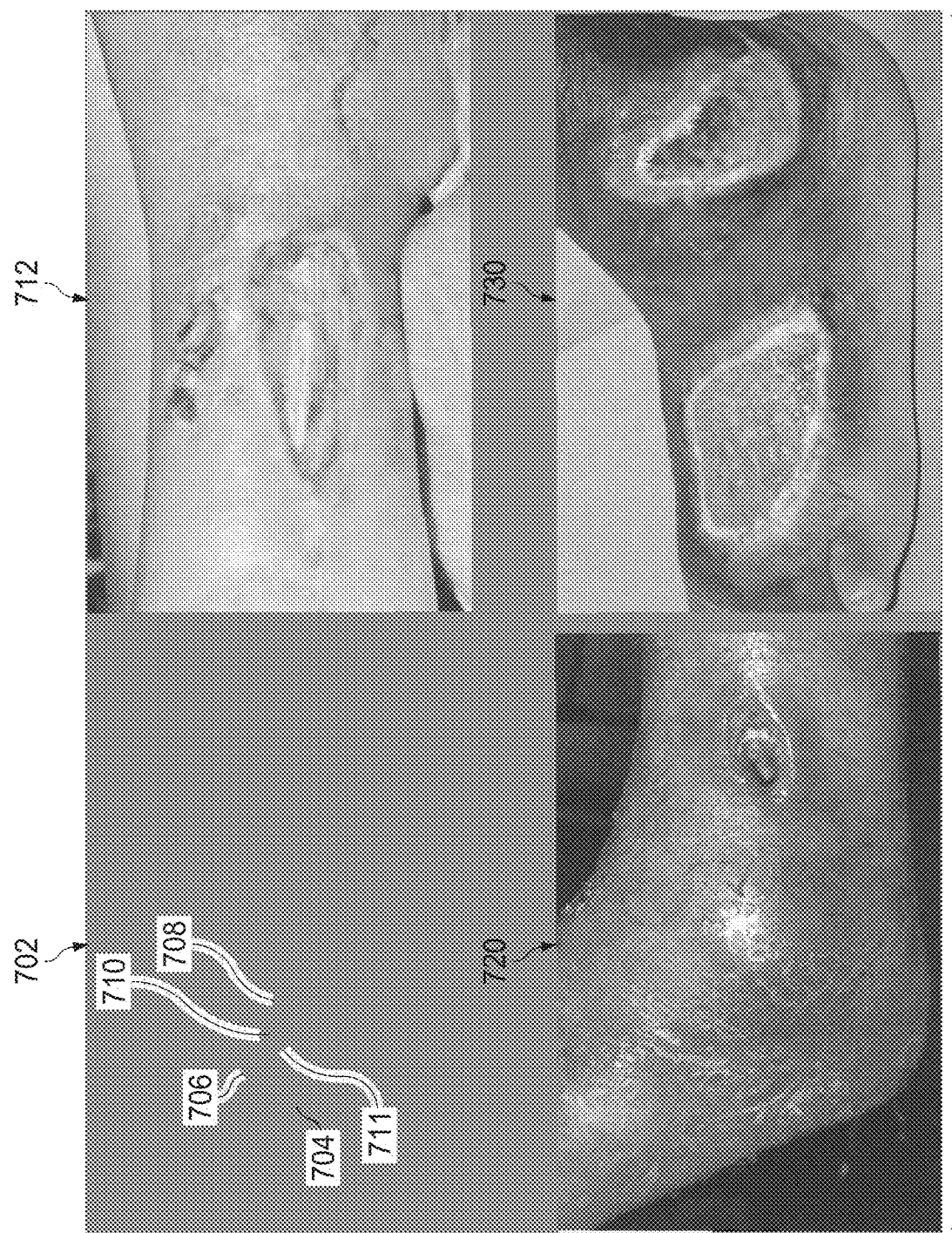
FIG. 7A shows views of example wound images which have properties that may confound simple wound tissue classification methods.

In practice, wound tissue classification may be rather complex. For example, while the wound 506 pictured in FIG. 5A had been freshly debrided and significant amounts of blood could be distinguished, FIG. 7A provides some example illustrations of wound images that may be more challenging for an automated skin filter operator to classify. For example, the views 702 and 712 of FIG. 7A illustrate wound images that may include multiple separate wound beds in the same image frame. Additionally, to further compound required classification analysis, each wound bed in a single image frame may include a variety of tissue types. For example, as shown in the views 702 and 712, multiple different skin layers 704 and 706 may be seen as well as underlying soft tissue 708. Further, portions of connective tissue 710, including tendons and ligaments, may be part of the image frame, in addition to segments of bone 711. Furthermore, as illustrated in view 720 and view 730, in some cases it may be difficult to accurately distinguish between an area of a wound and the surrounding healthy skin due to the coloring and/or texture of a peri-wound area being inconsistent with the surrounding healthy skin. In other words, some wound image frames may present rather complex and/or unique challenges for wound perimeter identification.

Figure 7B:
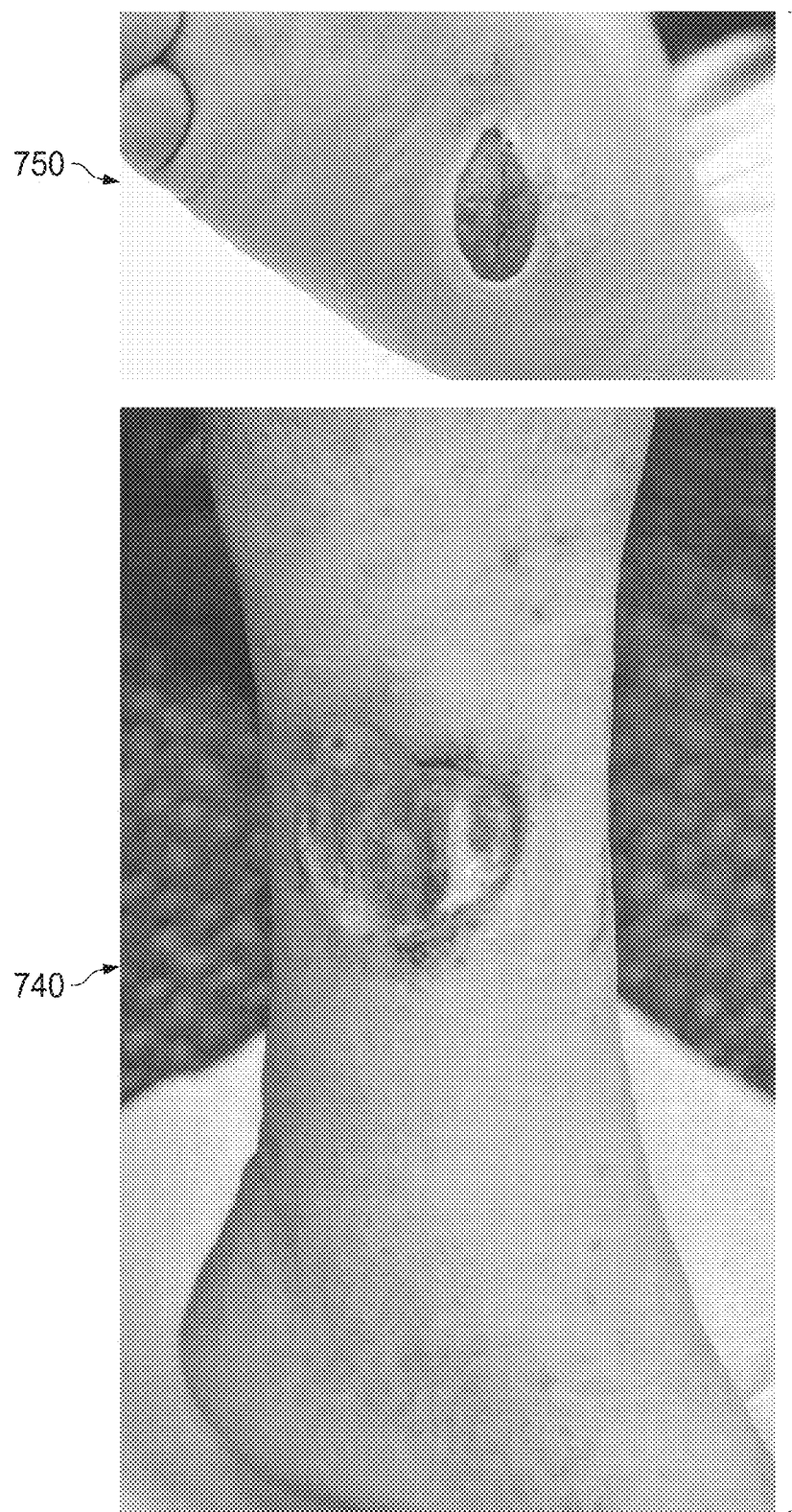
FIG. 7B shows additional views of example wound images which have properties that may confound simple wound tissue classification methods.

FIG. 7B provides some additional example illustrations of wound image frames that may present challenges for an automated skin filter operator. For example, as shown in the views 740 and 750 of FIG. 7B, additional difficulties may arise in situations where the wound occupies only a small percentage of the wound image frame. Wound tissue that is not uniformly colored or textured, as well as irregular wound bed features, can also confound the automated skin filter operator.

To address the challenges presented in FIG. 7, as well as others not specifically illustrated, wound image processing algorithms may include multi-modal techniques for producing clinically-relevant wound tissue classifications. In some embodiments, such multi-modal techniques may include color and intensity classification at the pixel (or path of pixels) level, as well as other techniques cuing from higher-order properties, such as textural and structural features. For example, color and intensity classification for a group of pixels may be indicative of a wound perimeter and/or characteristics of regions within the wound (e.g., necrotic, healthy, etc.). Over time, changes in color and intensity classification may be indicative of changing characteristics of the wound. For example, these classifications may indicate that the wound perimeter is decreasing, a ratio of healthy wound tissue to unhealthy wound tissue is increasing or decreasing, etc.

Accurate identification of a wound perimeter may be difficult due to the large variety of possible sizes, shapes, contexts, and overall appearance of wounds. To address the challenges with properly identifying wound perimeters according to the principles of the present disclosure, active contours (or snakes) are one method that may be used as a tool for properly identifying the borders or edges of wounds. In these applications, active contours typically model (i.e., simulate) an elastic band that, when placed outside of the image object to be captured, collapse inward to "hug" the object periphery. Active contours, or snakes, may be framed as an iterative energy minimization problem, and are related to stochastic methods like simulated annealing. For example, when a simulated elastic band corresponding to an active contour is stretched, the band may be considered to be in a high energy state. In other words, the band will tend toward a resting, unstretched state. In the context of wound imaging, the active contour may be configured into an initial state outlining the perimeter of the wound, which may be designated as (e.g., stored as) the resting state of the active contour. In other words, the resting state of the active contour corresponds to the perimeter of the wound. The state of the active contour may be represented by an energy function that outputs energy values according to a current state of the active contour relative to the resting state. For example, an output of the energy function may be relatively high when the active contour is outside of the wound perimeter, corresponding to a stretched state. Conversely, an output of the energy function is relatively low when the active contour is near the wound perimeter, corresponding to an unstretched state. As such, the energy function may be designed to take into account image properties and features corresponding to a wound edge, perimeter, etc. to accurately output a value representative of the configuration of the active contour relative to actual wound perimeter.

For example, "energy minimization" refers to allowing the simulated elastic band corresponding to the active contour to return to the resting state. In other words, in the context of wound imaging, the elastic band may initially be stretched into an ellipse or other suitable shape enclosing the entire wound. Then, the simulated elastic band can be allowed to "snap" around the actual wound perimeter. For example, an iterative energy minimization process is applied to reduce the energy of the elastic band. More specifically, the iterative energy minimization process attempts to identify the actual pixels corresponding to the wound perimeter and, accordingly, identify the position of the active contour that would correspond to the wound perimeter. In one example, the iterative energy minimization process evaluates the energy function with respect to the pixel locations of the current position of the active contour and then analyzes regions around each of these pixels. For example, for a pixel at a given point P, the process determines whether moving the pixel to a different point within its respective region would reduce the overall energy of the active contour (i.e., whether the new point is closer to the actual wound perimeter as indicated by, for example, identified features corresponding to the wound perimeter). If so, then the corresponding portion of the active contour is moved to the new point within the region to reduce the overall energy of the active contour. The process is repeated for each pixel of the active contour until no further modifications will reduce the energy of the active contour.

In some embodiments, the snake may respond to internal and external "pressures" in order to find a low-energy state. Regularization parameters of curvature and smoothness may enforce physical properties of the elastic band and may make the band resistant to breaking. External properties consistent with wound peripheries may be modeled such that they represent low-energy states. For example, multiple low-level parameters may be suggested in the wound image of FIG. 5A, such as red pixels, as well as pixels strong in magenta and yellow, however not cyan. Additionally, the gradient images, such as those pictured in FIG. 5C, may suggest that higher-order structures based on gradients in image intensity may be useful. Typically, in practice, the external properties that shape the snake are usually chosen under statistical guidance.

Figure 8A:
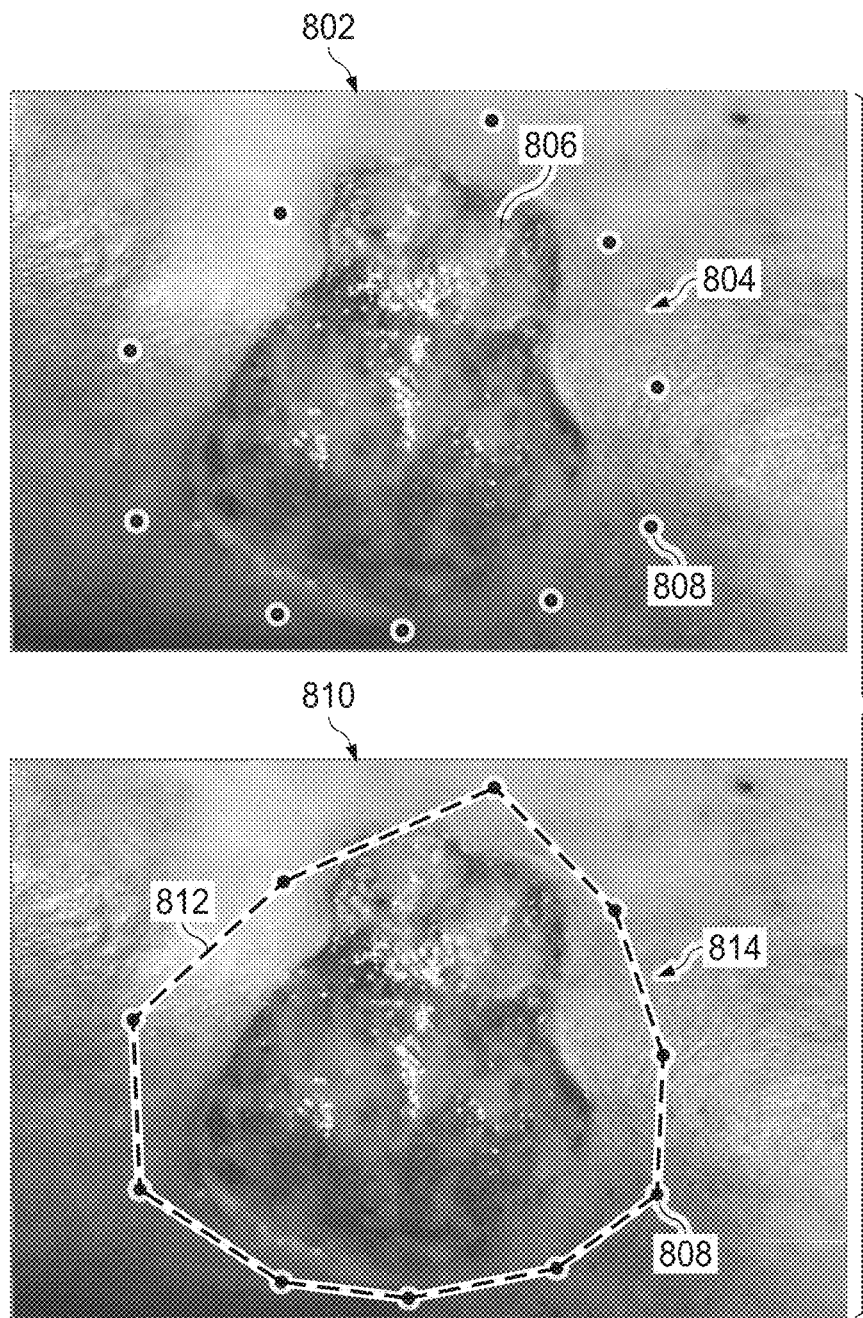

Referring now collectively to FIG. 8, an illustrative embodiment of the process of applying active contours to obtain high-fidelity wound perimeters is shown. As shown in first view 802 of FIG. 8A, a user of the image processing software may touch the image 804 around a wound 806 to set a variable number of control points 808 (or, in some examples, draw or trace a continuous line) in order to establish an initial, rough outline around the wound (e.g., a rough-bounding polygon). As illustrated in the second view 810 of FIG. 8A, the user may then double-tap the screen in order to initialize the automatic active contour lines 812 from the provided control points 808, creating an initial active contour, or snake, 814 from the user-provided control points 808.

Following now to FIG. 8B, the process of iterative convergence of the initial snake 814 may be shown in the example illustrations. Once the initial contour of the snake 814 has been identified, the image processing software may statistically analyze regions of the image outside of the active contour and compare them to regions within the contour. In this manner, the software may be able to automatically refine the snake 814 to more closely track the perimeter 822 of the wound 806, as shown in the first view 820 of FIG. 8B. The image processing software's interface, such as the touchscreen GUI 200 may allow the user to adjust the snake 814 through tap-and-drag gestures. For example, in some embodiments, the touchscreen GUI 200 may allow the user to select and unselect regions, expand and contract portions of the snake 814, as well as other interactive and guided adjustments. In some embodiments, a double-tap on the touchscreen GUI 200 by the user may commit the user's rough measurement of the perimeter 822 of the wound 806. Additionally, in some embodiments, the image processing software may permit the user to select between a contractive snake, as depicted in FIGS. 8-12, and an inflationary snake. For example, an inflationary snake may refer to a snake in which the contour is initialized with a single tap within the interior of the wound 806. This form of snake may then be expanded to identify the wound perimeter during energy minimization. The use of an inflationary snake may be particularly appropriate for smaller, symmetric wounds, such as many diabetic foot ulcers.

Figure 8D:
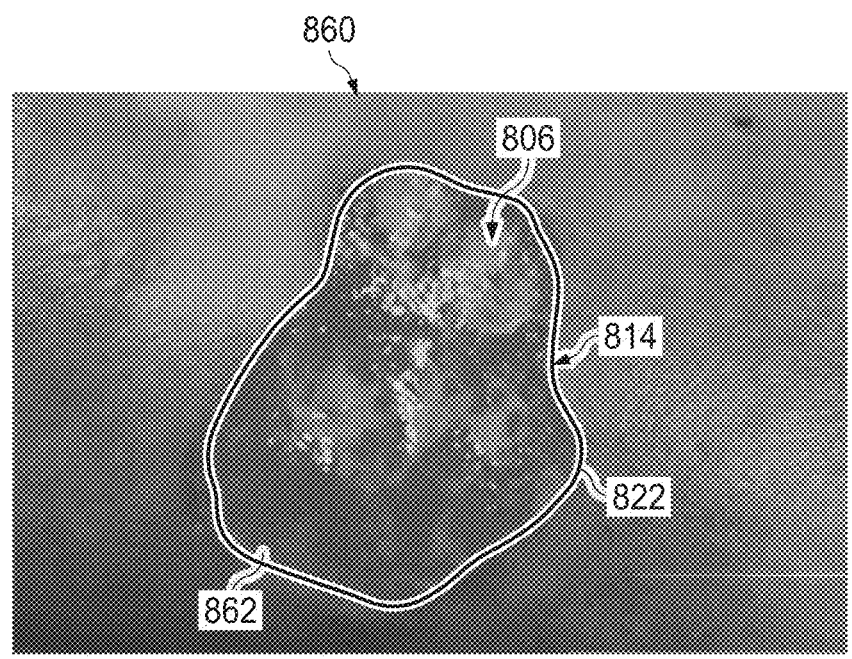

The first view 820 of FIG. 8B illustrates how after approximately 75 iterations of active contour processing, the snake 814 has converged to the upper perimeter 824 of the wound 806. Further, after approximately 150 iterations, as shown in the second view 830 of FIG. 8B, the snake 814 has converged to most of the perimeter 822 of wound 806. Continuing with FIG. 8C, further steps of the iterative convergence process of the snake 814 may be seen. Thus, the first view 840 of FIG. 8C shows how, after 225 iterations, the snake 814 has converged to almost all of the perimeter 822 of the wound 806, while the second view 850 of FIG. 8C illustrates how, after 261 iterations, the snake 814 has converged essentially entirely to the perimeter 822 of wound 806. FIG. 8D shows the same example wound 806 with the snake 814 locked onto the perimeter 822 of the wound 806 and stabilized. In the example view 860, the perimeter 822 of the wound 806 is highlighted in blue by the image processing software, and the wound interior 862 is highlighted in red. In this particular example image, the area of the shaded region, which corresponds to the wound interior 862, is 171,448 pixels.

Figure 9:
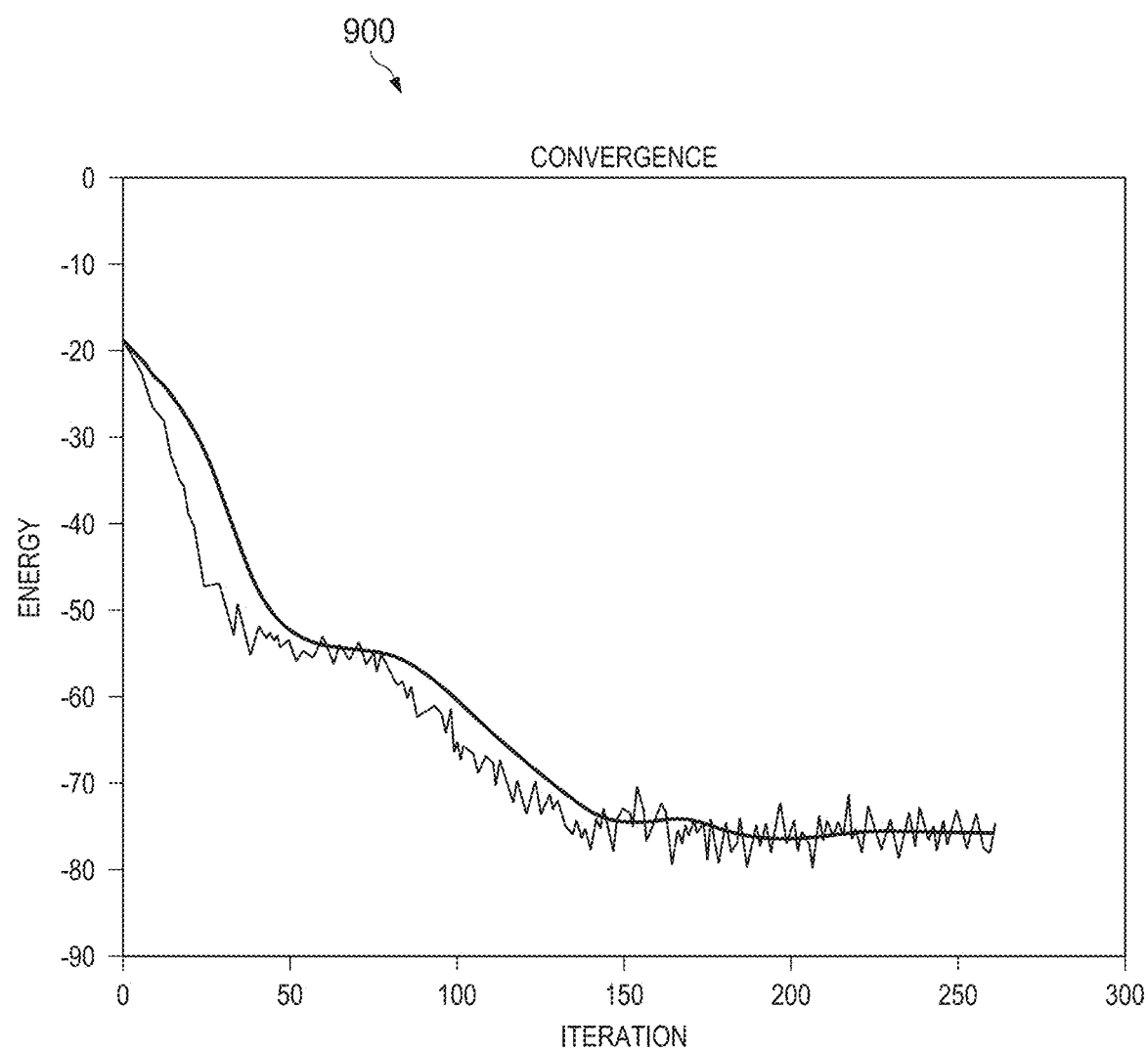
FIG. 9 shows a graphical illustration of the progress of the exemplary image processing method for the example wound image of FIGS. 8A-8D.

As shown in FIG. 9, throughout the iterative convergence process (e.g., an iterative energy minimization process as described above), the degree of convergence may be charted and tracked in order to determine when convergence has been completed. For example, the graph 900 of FIG. 9 shows that convergence is indicated when the smoothed contour energy stabilizes. Thus, FIG. 9 illustrates a depiction of an energy minimization sequence of the snake 814. When convergence is complete (and, therefore, the active contour is in the resting state corresponding to the wound perimeter), the user may further modify the position of the active contour using the touchscreen. For example, if the user recognizes that a portion of the active contour is not consistent with the actual wound perimeter, the user may use the touch screen (e.g., using tap-and-drag gestures) to adjust the active contour accordingly. The iterative convergence process may then be repeated using this feedback.

Figure 10A:
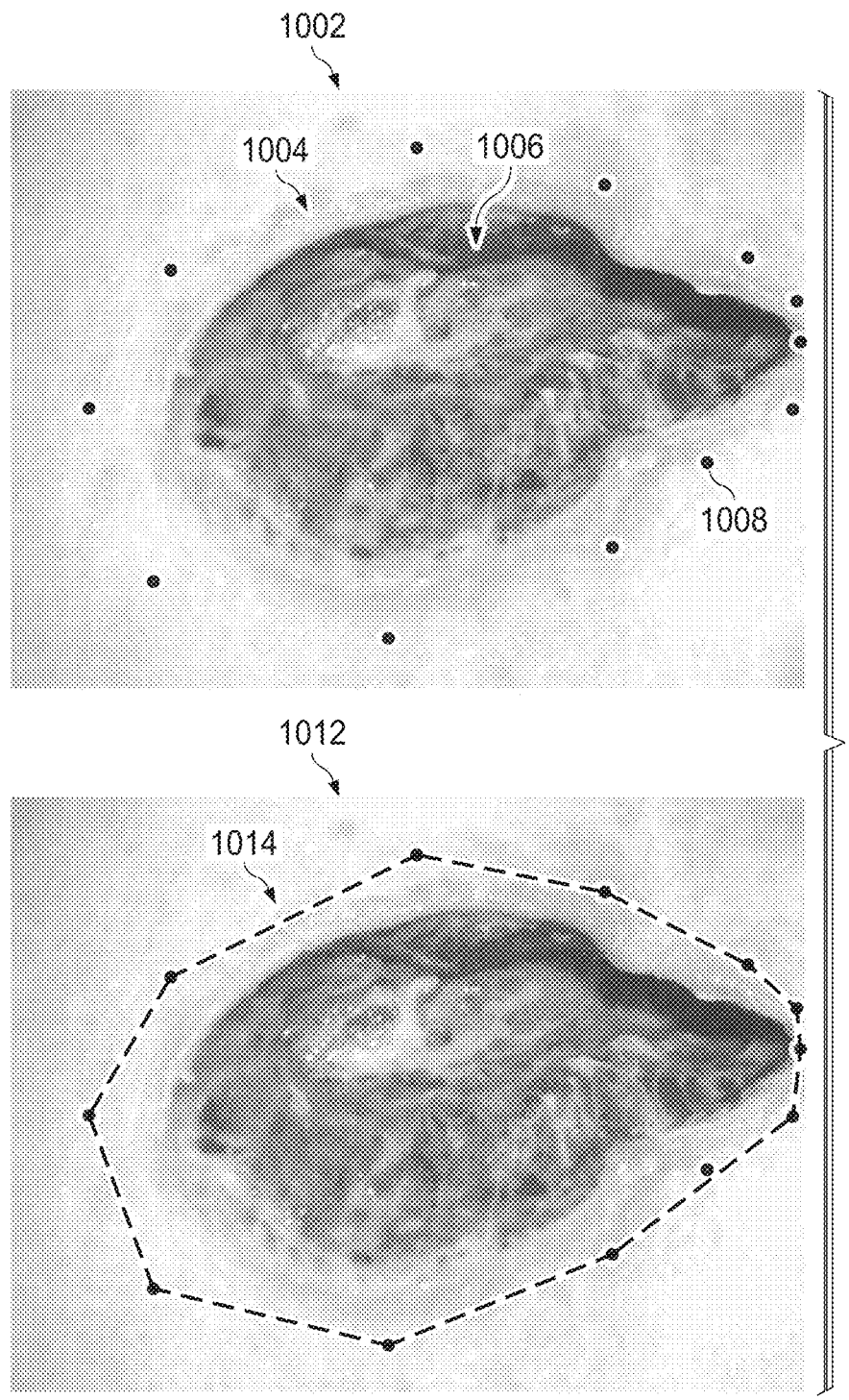
Figure 10C:
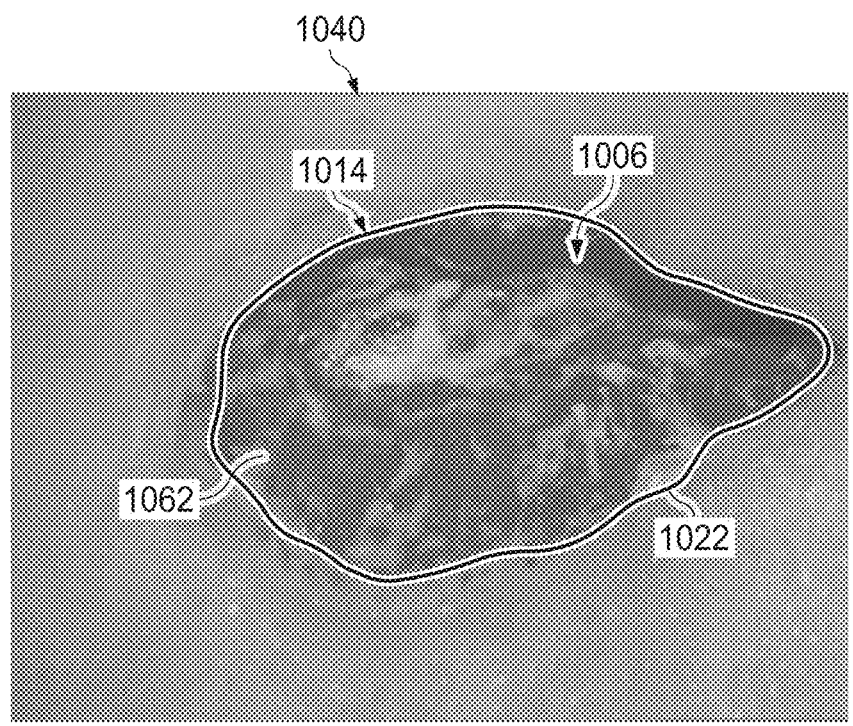
Figure 11:
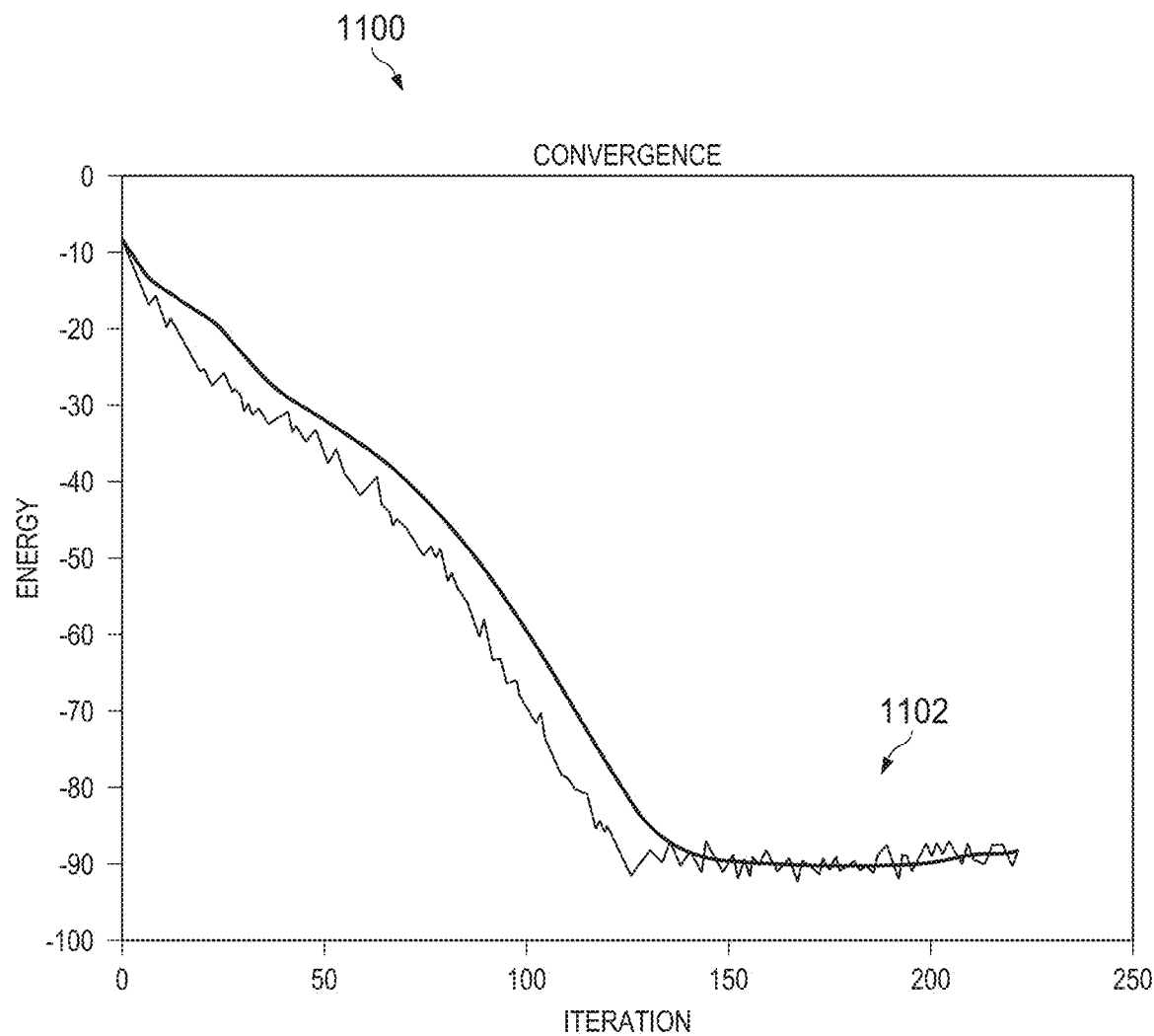
FIG. 11 shows a graphical illustration of the progress of the exemplary image processing method for the example wound image of FIGS. 10A-10C.

FIG. 10, collectively, illustrates an additional example of the image processing software's capability of applying the iterative convergence process to a wound image 1004. The wound image 1004 shown in FIG. 10, collectively, may be an image of a wound 1006. As shown in a first view 1002 of FIG. 10A, a user has tapped the touchscreen displaying a GUI 200 in order to set a variable number of control points 1008 in order to establish an initial snake 1014, as shown in the second view 1012 of FIG. 10A. FIG. 10B illustrates how once the user has double-tapped the touchscreen displaying the GUI 200, the automated wound perimeter identification functionality of the image processing software may be activated. As shown by comparing FIGS. 10A and 10B, the initial snake 1014 of FIG. 10B was created from the user-provided points 1008 in FIG. 10A. The first and second views, 1020 and 1030, respectively, of FIG. 10B show the progress of the convergence of the snake 1014 to the perimeter 1022 of the wound 1006 after approximately 75 iterations and 150 iterations, respectively. As shown in the first view 1020 of FIG. 10B, the active contour of the snake 1014 has converged uniformly to the perimeter 1022 of the wound 1006, while the second view 1030 of FIG. 10B shows how the active contour of the snake 1014 has converged to most of the perimeter 1022 of the wound 1006. FIG. 10C illustrates the continued steps of the active contour convergence process. For example, the view 1040 of FIG. 10C illustrates how after 235 iterations of active contour processing, the snake 1014 has locked onto the perimeter 1022 of the wound 1006 and has been stabilized. In some embodiments, the perimeter 1022 of the wound 1006 may be highlighted in blue, and the interior 1062 of the wound 1006 may be highlighted in red. For example, in this illustrative example, the area of the shaded region corresponding to the interior 1062 of the wound 1006 has a size of 228,627 pixels. Similar to FIG. 9, FIG. 11 illustrates how convergence may be graphically indicated, when the smoothed contour energy stabilizes, as shown in region 1102 of the graph 1100.

Figure 12A:
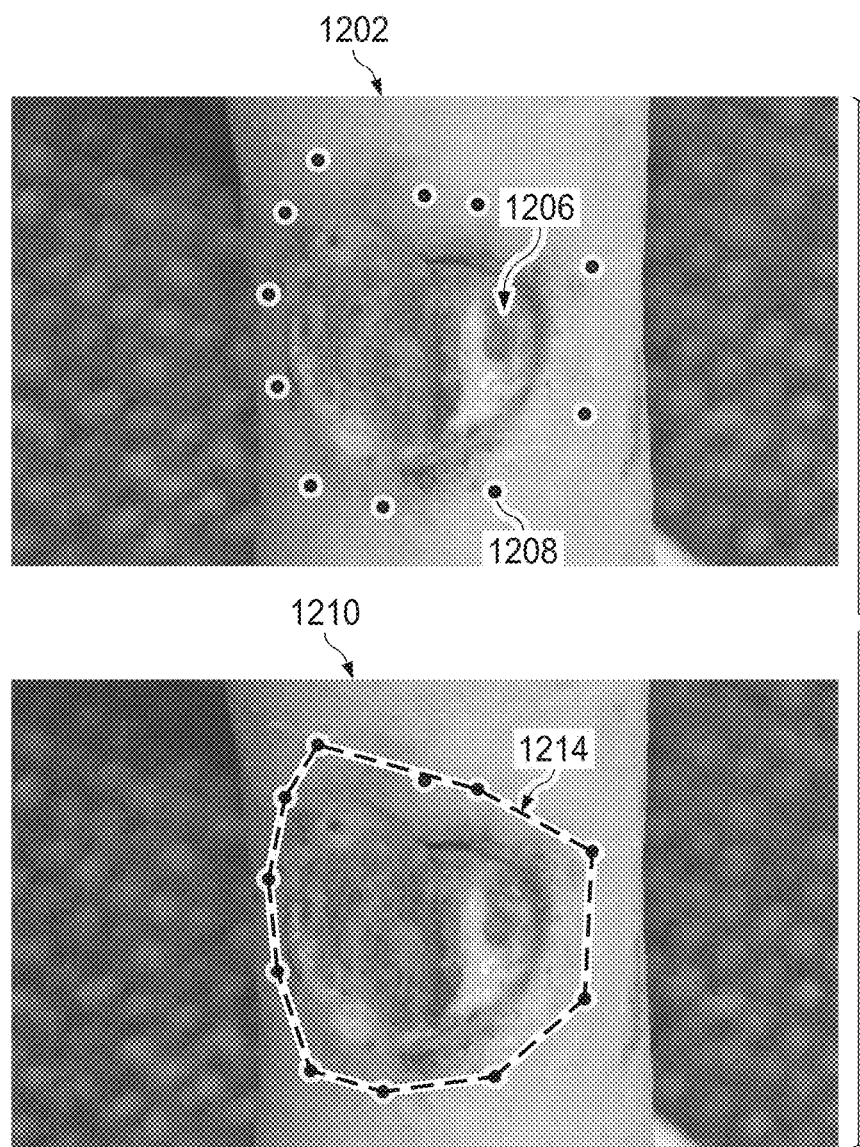
FIGS. 12A-12C illustrate example views associated with an exemplary image processing method in accordance with the specification for an example wound image.
Figure 12B:
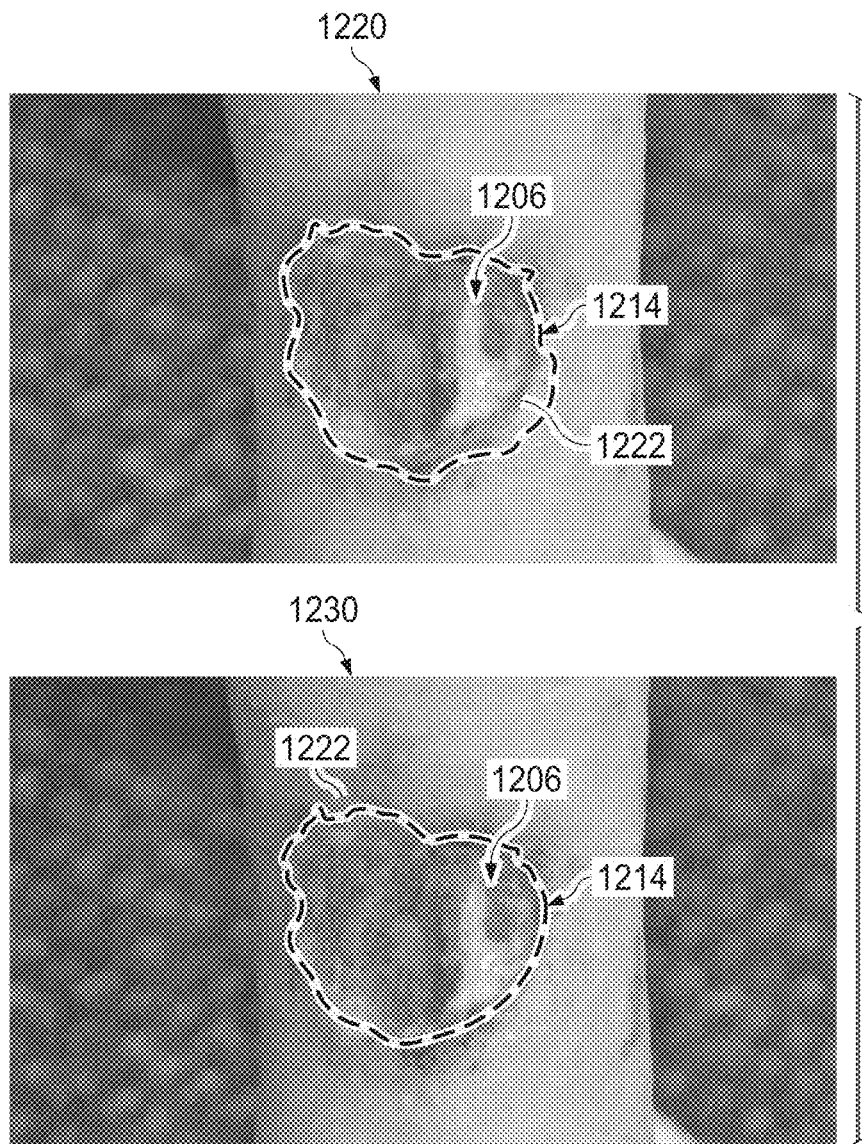
Figure 12C:
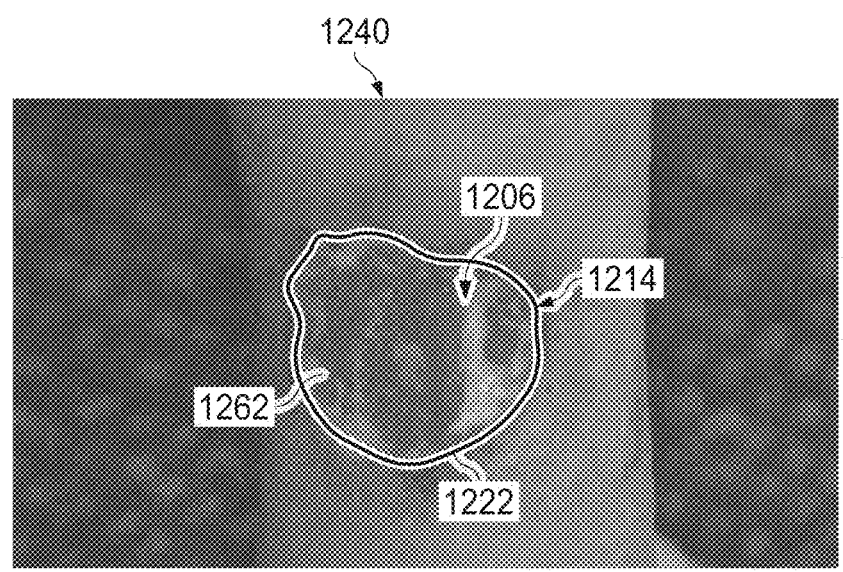
Figure 13:
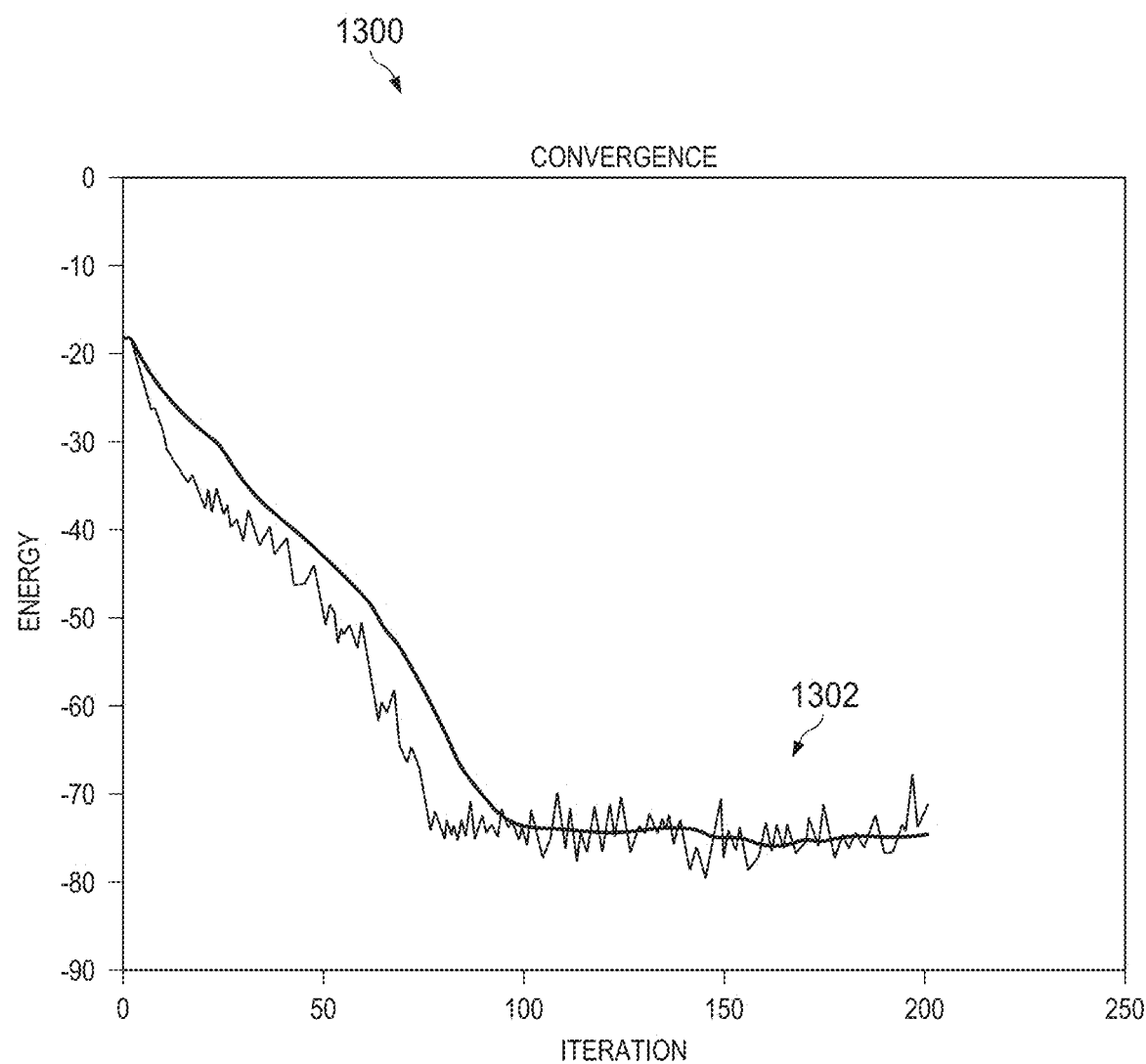
FIG. 13 shows a graphical illustration of the progress of the exemplary image processing method for the example wound image of FIGS. 12A-12C.

FIG. 12, collectively, illustrates yet another example of the iterative convergence process of the image processing software, applied to a wound 1206. Similarly to the examples discussed with respect to FIGS. 8 and 10, the user may tap the touchscreen displaying a GUI 200 in order to set a variable number of control points 1208 for establishing a rough-bounding polygon, as illustrated in the first view 1202 of FIG. 12A. The user may then double-tap the touchscreen to activate the automated wound perimeter identification functionality of the image processing software, and to generate the snake 1214, as shown in the second view 1210. The first and second views, 1220 and 1230, respectively, of FIG. 12B once again illustrate the progress of the convergence of the snake 1214 to the perimeter 1222 of the wound 1206 after 75 and 150 iterations, respectively. Now referring to FIG. 12C, the view 1240 shows how, in this illustrative example, the snake 1214 has locked onto the perimeter 1222 of the wound 1206 and has been stabilized. Similar to the examples of FIGS. 8 and 10, the perimeter 1222 of the wound 1206 may be highlighted in blue, and the interior 1262 of the wound 1206 may be highlighted in red. In this illustrative example, the area of the shaded region corresponding to the interior 1262 of the wound 1206 includes 66,075 pixels, thus indicating that the area of the wound 1206 may be considerably smaller than that of the wounds 806 and 1006 of FIGS. 8 and 10, respectively. Once again, the convergence of the snake 1214 may be graphically indicated by noticing when the smoothed contour energy stabilizes as shown in region 1302 of the graph 1300 of FIG. 13.

Figure 14:
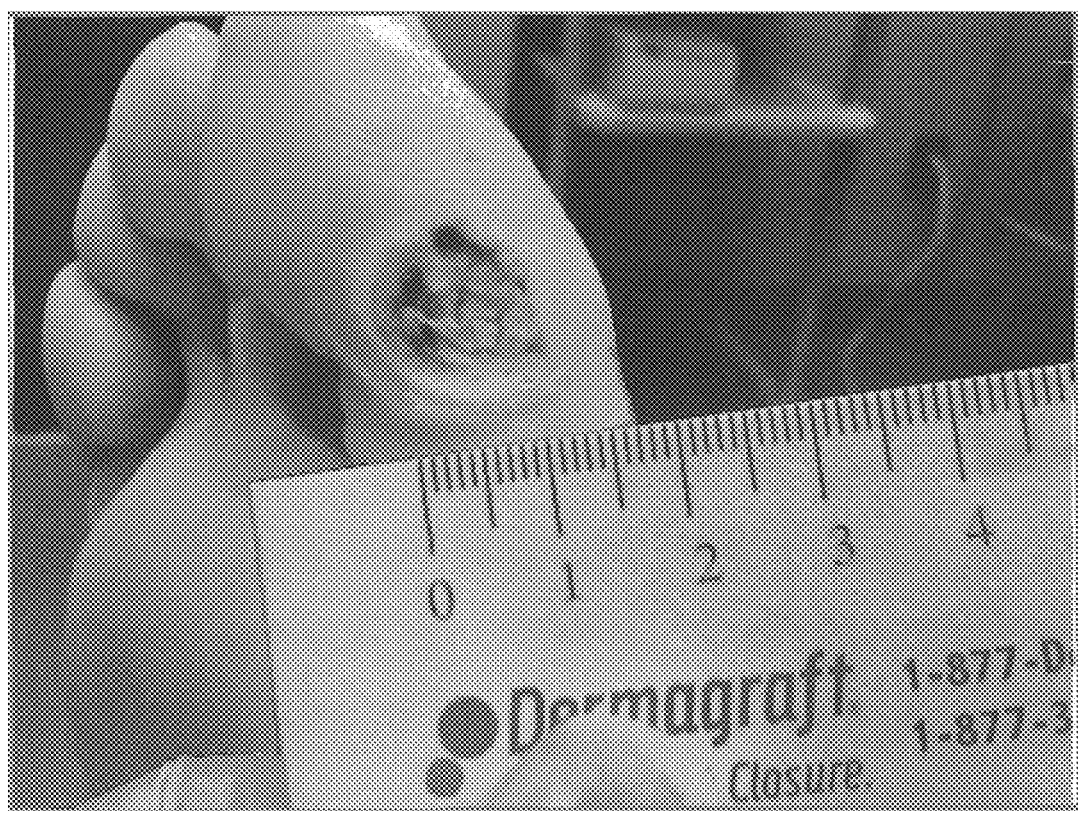
FIG. 14 illustrates a view of the result of an image filter applied to an example wound image for identifying the extents of a wound ruler.

As indicated with respect to the explanation of FIGS. 8-13, the process for identifying the perimeter of a wound may provide an estimate of the wound area in units of square pixels. In order to transform this area measurement from square pixels into a clinically-relevant measure of centimeters, the image processing software may also be equipped with the capacity for detecting and using image scale-identification markers. For example, an example of an image scale-identification marker may be the 2 cm×2 cm square on a wound ruler, which may be available from Kinetic Concepts Inc., of San Antonio, Tex. The marker may have a shape that facilitates identification of the size of the image (e.g., a square, such as a square with 2 cm sides) while also facilitating conversion to different size units. Using such a marker, the image processing software may be able to transform pixel area measurements into real-world measurements. For example, the marker may be sized such that a predetermined amount of pixels fit within the marker, and each pixel (or string of pixels) is correlated to a real-world measurement. For example only, 200 pixels may correspond to 2 cm. Referring now to FIG. 14, the result of the use of an image filter to automatically identify the extents of a wound ruler may be seen. Additionally, the image processing software may allow the user to refine the marker identification, as potentially required. For example, characteristics such as size and color of the scale marker preferably allow the scale marker to be more easily distinguishable from the image itself.

In addition to the examples of the previously-discussed figures, there are a number of algorithms as well as techniques that may be used to improve or refine automated wound periphery measurements. For example, advanced classification methods, such as support vector machines (SVMs) may be used. Additionally, artificial neural networks (ANNs) may also be applied to assist with refining the wound periphery measurements. In some embodiments, additional algorithms and techniques may be used to assist with wound segmentation. For example, a variety of probabilistic algorithms may also be utilized. Alternatively or additionally, wound texture analysis may be used to aid with wound segmentation. Such wound texture analysis techniques may include gray-level co-occurrence matrix (GLCM), wavelets, as well as other processes. As an example, a technique such as GLCM and/or wavelets may be used to identify certain features of a wound image such as textures, edges, etc., while techniques such as SVMs and/or ANNs may be used to analyze those identified features to determine wound regions. In one example, the identified features may correspond to regions that are red and not smooth, while further processing performed by an SVM, ANN, etc. classifies regions having those features as wound regions (i.e., correlating red and not smooth features to a wound region rather than healthy skin).

Embodiments of the wound imaging and diagnostic application may be further customized to include additional functional modules for offering further capabilities and services to users of the application. For example, one or more functional modules related to wound imaging may be integrated. The wound imaging and diagnostic application may also include training modules, which may be configured to offer clinicians tutorials on utilizing the application as well as training videos for processing more complex tissue sites. Links to external reference guides may also be provided via links in the application in order for ease of use.

The systems, apparatuses, and methods described herein may provide significant advantages. Currently, widely-practiced manual technologies and methods for wound area assessment are known to be subjective and often yield coarse estimates of wound area. For example, as previously mentioned, color is a prime indicator of wound healing that is commonly used in clinical settings. However, one problem with using color-identification is that color appearance can often be altered depending on lighting conditions. For example, a wound under incandescent lighting may have a very different color appearance from a wound under fluorescent lighting. Furthermore, different clinicians may have different degrees of color perception. For example, while one clinician may have strong color perception, another clinician may be color blind in one or more colors, thereby creating a situation where the two clinicians construe different interpretations of the color, and therefore type, of wound tissue.

Furthermore, the systems and methods described herein may offer particular advantages over current techniques for identifying and measuring different types of wound tissue. For example, one current technique includes placing a clear film over a wound and using a soft-tipped pen to color different wound tissues on the film, thereby making a record of the wound tissues. This process may be repeated to record wound healing over time. However, this process often suffers due to lighting conditions, color sensitivity of clinicians, limitations of the ability of a clinician to accurately draw on the clear film, and inherent problems associated with contacting the film onto the wound tissue. Another technique includes making an outline of the wound on the film, scanning the image into a computer, and then drawing an estimation of the different wound tissue on the computer. However, this technique also suffers from inaccuracy.

In contrast, calibrated, automated image processing systems and methods, such as the systems and methods described herein may increase wound area measurement accuracy. While current practice involves probing the wound bed to determine wound depth, which often can lead to pain or discomfort for the patient, using a three-dimensional camera to image the wound can automatically calculate many of these dimensions. As a result, much of the need for making physical contact with the wound may be avoided. Given these observations, as well as the widespread use of smartphones and tablets that are equipped with high-resolution cameras and robust, multi-core processors, the opportunity exists for developing a platform for improving in-field wound care. As such, a convenient and intuitive wound imaging and analysis system can reduce subjectivity and improve efficiency in routine wound assessment. Furthermore, the benefits of the present invention may be substantially scaled should the invention be applied in a telemedicine wound management program.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A non-transitory computer-readable medium comprising executable code, wherein the executable code comprises:
   receiving, at an active contouring module, a wound image;
   identifying, at the active contouring module, features of the wound image on opposite sides of an initial outline of a wound; and
   calculating an actual perimeter of the wound based on the initial outline of the wound and the identified features of the wound image.

2. The non-transitory computer-readable medium of claim 1, wherein the executable code further comprises:
   generating a graphical representation of the actual perimeter of the wound for output to a display screen.

3. The non-transitory computer-readable medium of claim 1, wherein the executable code further comprises:
   calculating a wound area based on the actual perimeter of the wound.

4. The non-transitory computer-readable medium of claim 1, wherein the executable code further comprises:
   identifying a number of pixels enclosed by the actual perimeter of the wound;
   detecting an image-scale identification marker present in the wound image;
   identifying a size of each pixel based on the image-scale identification marker; and
   calculating a wound area based on the number of pixels enclosed by the actual perimeter of the wound.

5. The non-transitory computer-readable medium of claim 1, wherein the executable code further comprises:
   initializing an active contour model by defining the initial outline of the wound as an initial active contour;
   performing an iterative energy minimization process on the initial active contour to determine a final active contour; and
   storing the final active contour as the actual perimeter of the wound.

6. The non-transitory computer-readable medium of claim 5, wherein the executable code further comprises:
   converting the wound image from an RGB color space to a CMYK color space; and
   decomposing the wound image into a magenta component and a yellow component.

7. The non-transitory computer-readable medium of claim 6, wherein the executable code further comprises:
   defining the magenta component as a low-energy state in the iterative energy minimization process.

8. The non-transitory computer-readable medium of claim 6, wherein the executable code further comprises:
   defining the yellow component as a low-energy state in the iterative energy minimization process.

9. The non-transitory computer-readable medium of claim 1, wherein the executable code further comprises:
   creating a gradient image in an x-direction from the wound image; and
   calculating the actual perimeter of the wound by identifying areas of high gradient from the gradient image.

10. The non-transitory computer-readable medium of claim 1, wherein the executable code further comprises:
    creating a gradient image in a y-direction from the wound image; and
    calculating the actual perimeter of the wound by identifying areas of high gradient from the gradient image.

11. A method for processing a wound image, comprising:
    receiving, at an active contouring module, the wound image;

identifying, at the active contouring module, features of the wound image on opposite sides of an initial outline of a wound; and calculating an actual perimeter of the wound based on the initial outline of the wound and the identified features of the wound image.

12. The method of claim 11, further comprising:

generating a graphical representation of the actual perimeter of the wound for output to a display screen.

13. The method of claim 11, further comprising:

calculating a wound area based on the actual perimeter of the wound.

14. The method of claim 11, further comprising:

identifying a number of pixels enclosed by the actual perimeter of the wound;

detecting an image-scale identification marker present in the wound image;

identifying a size of each pixel based on the image-scale identification marker; and calculating a wound area based on the number of pixels enclosed by the actual perimeter of the wound.

15. The method of claim 11, further comprising:

initializing an active contour model by defining the initial outline of the wound as an initial active contour;

performing an iterative energy minimization process on the initial active contour to determine a final active contour; and storing the final active contour as the actual perimeter of the wound.

16. The method of claim 15, further comprising:

converting the wound image from an RGB color space to a CMYK color space; and decomposing the wound image into a magenta component and a yellow component.

17. The method of claim 16, further comprising:

defining the magenta component as a low-energy state in the iterative energy minimization process.

18. The method of claim 16, further comprising:

defining the yellow component as a low-energy state in the iterative energy minimization process.

19. The method of claim 11, further comprising:

creating a gradient image in an x-direction from the wound image; and calculating the actual perimeter of the wound by identifying areas of high gradient from the gradient image.

20. The method of claim 11, further comprising:

creating a gradient image in a y-direction from the wound image; and calculating the actual perimeter of the wound by identifying areas of high gradient from the gradient image.

* * * * *